US008126738B2

(12) United States Patent
Green et al.

(10) Patent No.: US 8,126,738 B2
(45) Date of Patent: Feb. 28, 2012

(54) METHOD AND SYSTEM FOR SCHEDULING TRACKING, ADJUDICATING APPOINTMENTS AND CLAIMS IN A HEALTH SERVICES ENVIRONMENT

(75) Inventors: Jason Reinis Green, Jacksonville, FL (US); Raymond Michael Wood, Jacksonville, FL (US); Robert John Snyder, St. Augustine, FL (US); Richard R. Willich, St. Augustine, FL (US)

(73) Assignee: MDI Technologies, Inc., Ponte Vedra, FL (US)

( * ) Notice: Subject to any disclaimer, the term of this patent is extended or adjusted under 35 U.S.C. 154(b) by 1145 days.

(21) Appl. No.: 11/412,836

(22) Filed: Apr. 28, 2006

(65) Prior Publication Data

US 2007/0255586 A1  Nov. 1, 2007

(51) Int. Cl.
*G06Q 50/00* (2006.01)
*G06Q 40/00* (2006.01)

(52) U.S. Cl. ............................................... 705/3; 705/4
(58) Field of Classification Search .................... 705/2–4
See application file for complete search history.

(56) References Cited

U.S. PATENT DOCUMENTS

| | | | |
|---|---|---|---|
| 5,235,702 A | 8/1993 | Miller | |
| 5,253,164 A | 10/1993 | Holloway et al. | |
| 5,301,105 A | 4/1994 | Cummings, Jr. | |
| 5,359,509 A | 10/1994 | Little et al. | |
| 5,550,734 A * | 8/1996 | Tarter et al. | 705/2 |
| 5,778,882 A | 7/1998 | Raymond et al. | |
| 5,822,741 A | 10/1998 | Fischthal | |
| 5,970,463 A | 10/1999 | Cave et al. | |
| 6,032,119 A | 2/2000 | Brown et al. | |
| 6,067,523 A * | 5/2000 | Bair et al. | 705/3 |
| 6,112,183 A | 8/2000 | Swanson et al. | |
| 6,208,974 B1 | 3/2001 | Campbell et al. | |
| 6,289,316 B1 | 9/2001 | Aghili et al. | |
| 6,314,405 B1 | 11/2001 | Richardson | |

(Continued)

FOREIGN PATENT DOCUMENTS

WO    WO 00/34897 A1    6/2000

(Continued)

OTHER PUBLICATIONS

U.S. Patent Office Action dated Dec. 13, 2007, in U.S. Appl. No. 11/449,724.

(Continued)

*Primary Examiner* — Sheetal R Rangrej
(74) *Attorney, Agent, or Firm* — Williams Mullen, PC; Thomas F. Bergert

(57) ABSTRACT

An exemplary method for determining the appropriateness of service provider claims for payment includes scheduling appointments for patients with service providers based on requests for services, generating appointment information corresponding to each of the scheduled appointments, and capturing service information corresponding to claims received from the service providers for payment of charges associated with services rendered by the service providers to the patients. The method further includes automatically identifying candidate appointments that correspond to a particular received claim based on a degree of similarity between the service information associated with the particular received claim and the appointment information associated with the scheduled appointments. Additionally, the method includes flagging the particular received claim for resolution when none of the candidate appointments corresponds to the particular received claim, and presenting the particular received claim for payment when at least one of the candidate appointments corresponds to the particular received claim.

61 Claims, 33 Drawing Sheets

U.S. PATENT DOCUMENTS

| | | | |
|---|---|---|---|
| 6,324,516 B1 | 11/2001 | Shults et al. | |
| 6,341,265 B1 | 1/2002 | Provost et al. | |
| 6,343,271 B1 | 1/2002 | Peterson et al. | |
| 6,363,393 B1 | 3/2002 | Ribitzky | |
| 6,370,511 B1 | 4/2002 | Dang | |
| 6,374,229 B1 | 4/2002 | Lowrey et al. | |
| 6,684,276 B2 | 1/2004 | Walker et al. | |
| 6,792,410 B1 | 9/2004 | Donovan et al. | |
| 6,826,536 B1 | 11/2004 | Forman | |
| 6,879,959 B1 | 4/2005 | Chapman et al. | |
| 7,003,730 B2 | 2/2006 | Dettinger et al. | |
| 7,089,592 B2 | 8/2006 | Adjaoute | |
| 7,107,547 B2 | 9/2006 | Cule et al. | |
| 7,194,416 B1 | 3/2007 | Provost et al. | |
| 7,263,492 B1 | 8/2007 | Suresh et al. | |
| 7,490,100 B2 | 2/2009 | Dettinger et al. | |
| 2002/0004729 A1 | 1/2002 | Zak et al. | |
| 2002/0032582 A1 | 3/2002 | Feeney, Jr. et al. | |
| 2002/0052763 A1 | 5/2002 | Jung Richardson | |
| 2002/0138306 A1 | 9/2002 | Sabovich | |
| 2003/0069760 A1 | 4/2003 | Gelber | |
| 2003/0135397 A1 | 7/2003 | Halow et al. | |
| 2003/0146942 A1 | 8/2003 | Helgason et al. | |
| 2003/0208379 A1 | 11/2003 | Haskey et al. | |
| 2004/0073456 A1 | 4/2004 | Gottlieb et al. | |
| 2004/0078227 A1 | 4/2004 | Morris | |
| 2004/0133452 A1 | 7/2004 | Denny, Jr. et al. | |
| 2004/0143454 A1 | 7/2004 | Kimmel | |
| 2004/0172313 A1 | 9/2004 | Stein et al. | |
| 2004/0230458 A1 | 11/2004 | Takayama et al. | |
| 2005/0137912 A1 | 6/2005 | Rao et al. | |
| 2005/0159983 A1* | 7/2005 | Sullivan | 705/2 |
| 2005/0261944 A1 | 11/2005 | Rosenberger | |
| 2005/0283387 A1 | 12/2005 | Donoghue et al. | |
| 2006/0004604 A1 | 1/2006 | White | |
| 2006/0026051 A1* | 2/2006 | Rose | 705/8 |
| 2006/0116913 A1* | 6/2006 | Hansan et al. | 705/4 |
| 2006/0149784 A1 | 7/2006 | Tholl et al. | |
| 2007/0055553 A1 | 3/2007 | Kwan | |
| 2007/0118410 A1 | 5/2007 | Nadai | |
| 2007/0168232 A1 | 7/2007 | Kimmel | |
| 2007/0255586 A1 | 11/2007 | Green et al. | |
| 2007/0255590 A1 | 11/2007 | Green et al. | |
| 2007/0255591 A1 | 11/2007 | Green et al. | |
| 2007/0255592 A1 | 11/2007 | Green et al. | |
| 2007/0260484 A1 | 11/2007 | Kimmel | |

FOREIGN PATENT DOCUMENTS

| | | |
|---|---|---|
| WO | WO 02/21313 A2 | 3/2002 |

OTHER PUBLICATIONS

Green et al., U.S. Appl. No. 11/979,528, filed Nov. 5, 2007, entitled "System and Method for Accessing Patient History Information in a Health Services Environment Using a Human Body Graphical User Interface".

U.S. Patent Office Action dated Dec. 13, 2007, in U.S. Appl. No. 11/449,724.

U.S. Patent Office Action dated Nov. 26, 2008, in U.S. Appl. No. 11/725,491.

U.S. Patent Office Action dated Nov. 28, 2008, in U.S. Appl. No. 11/449,722.

Green et al., U.S. Appl. No. 11/979,528, filed Nov. 5, 2007, entitled, "System and Method for Accessing Patient History Information in a Health Services Environment Using a Human Body Graphical User Interface".

Bloodhound Technologies Defines Real-Time with Convergence Point, Brochure, 2009, Bloodhound Technologies, Inc., Durham, NC.

McLaugn, Kim, "IBM develops 3D patient record software", www.reuters.com/article/email/idUSTRE52394X720090310.

Information Technology; Web-based revenue cycle management company signs agreement with physician group. Medical Devices & Surgical Technology Week [serial online], Mar. 2005, pp. 249.

"NYU Downtown Selects athenaCollector to Increase Revenues and Reduce Insurance Claim Submission Errors." Business Wire, Jul. 13, 2004, pp. 1.

"Paperless cure," Health Management Technology, Jul. 1, 2001: 26-27, vol. 22.

"scheduling.com and athenahealth.com Form Strategic Alliance to Provide Enterprise-Wide Healthcare Business Solution." PR Newswire, Dec. 12, 2000, pp. 1.

U.S. Patent Office Action dated Jun. 12, 2009, in U.S. Appl. No. 11/449,722.

U.S. Patent Office Action dated Mar. 30, 2010, in U.S. Appl. No. 11/449,722.

U.S. Patent Office Action dated Sep. 16, 2010, in U.S. Appl. No. 11/449,722.

U.S. Patent Office Action dated Jun. 3, 2008, in U.S. Appl. No. 11/449,724.

U.S. Patent Office Action dated Apr. 1, 2010, in U.S. Appl. No. 11/449,724.

U.S. Patent Office Action dated Aug. 20, 2010, in U.S. Appl. No. 1/449,724.

U.S. Patent Office Action dated Jun. 11, 2009, in U.S. Appl. No. 11/725,491.

Green et al., Appeal Brief dated Jan. 11, 2010 in U.S. Appl. No. 11/725,491.

U.S. Patent Office action dated Mar. 31, 2010, in U.S. Appl. No. 11/725,491.

Green et al., Appeal Brief dated Jun. 7, 2010 in U.S. Appl. No. 11/725,491.

U.S. Patent Office Action dated Sep. 2, 2010, in U.S. Appl. No. 11/725,491.

U.S. Patent Office Action dated Jun. 22, 2010, in U.S. Appl. No. 11/979,528.

* cited by examiner

Verifying Digital Claim

HIPAA Suite ID:

Claim Type: UB92

Bill Provider's State (Box 1): FL

Subscriber State (Box 38): FL

Patient's State (Box 13): FL

Date Received: 03/23/2006

Patient Last Name:

Patient First Name:

Patient's Birth Date: 05/30/1972

Gender: Male

Patient Control No (Box 3):

Date of Service From: 03/11/2006   To: 03/11/2006

Provider TaxID:

Claim Amount: $ 3,617.46 — 1191

[Save]  [Cancel]

| ID | View | PDF | Contract | Provider | EIN | Date of Service | Patient Number | Patient Last Name | Patient First Name | Amount | Priority | Scheduling |
|---|---|---|---|---|---|---|---|---|---|---|---|---|
| 16966 | SELECT | VIEW | | | | 12/27/2005 | | | | 143.00 | ☐ | ☐ |
| 16967 | SELECT | VIEW | | | | 12/27/2005 | | | | 151.00 | ☐ | ☐ |
| 17243 | SELECT | VIEW | 1201 | | | 12/29/2005 | | | | 117.00 | ☐ | ☐ |
| 17338 | SELECT | VIEW | | | | 12/20/2005 | | | | 20693.69 | ☐ | ☑ |
| 17550 | SELECT | VIEW | 1189 | | | 01/03/2006 | | | | 117.00 | ☐ | ☐ |
| 17551 | SELECT | VIEW | | | | 01/03/2006 | | | | 143.00 | ☐ | ☐ |
| 17552 | SELECT | VIEW | | | | 01/04/2006 | | | | 191.00 | ☐ | ☐ |
| 17735 | SELECT | VIEW | | | | 09/30/2005 | | | | 230.00 | ☐ | ☐ |
| 18012 | SELECT | VIEW | | | | 11/25/2005 | | | | 2280.00 | ☐ | ☐ |
| 18320 | SELECT | VIEW | | | | 12/06/2005 | | | | 127.00 | ☐ | ☐ |
| 18322 | SELECT | VIEW | | | | 12/08/2005 | | | | 293.00 | ☐ | ☐ |
| 18325 | SELECT | VIEW | | | | 12/02/2005 | | | | 195.00 | ☐ | ☐ |
| 18326 | SELECT | VIEW | | | | 12/06/2005 | | | | 210.00 | ☐ | ☐ |
| 18327 | SELECT | VIEW | | | | 12/14/2005 | | | | 144.00 | ☐ | ☐ |
| 18328 | SELECT | VIEW | | | | 12/09/2005 | | | | 34.00 | ☐ | ☐ |
| 18329 | SELECT | VIEW | | | | 12/22/2005 | | | | 144.00 | ☐ | ☐ |
| 18937 | SELECT | VIEW | | | | 12/20/2005 | | | | 55.00 | ☐ | ☐ |
| 18938 | SELECT | VIEW | | | | 12/20/2005 | | | | 210.00 | ☐ | ☐ |
| 18954 | SELECT | VIEW | | | | 01/12/2006 | | | | 144.00 | ☐ | ☐ |
| 19118 | SELECT | VIEW | | | | 01/12/2006 | | | | 151.00 | ☐ | ☐ |
| 19119 | SELECT | VIEW | | | | 01/12/2006 | | | | 240.00 | ☐ | ☐ |
| 19260 | SELECT | VIEW | | | | 12/14/2005 | | | | 144.00 | ☐ | ☐ |
| 19306 | SELECT | VIEW | | | | 01/17/2006 | | | | 127.00 | ☐ | ☐ |

Number of Records: 178

FIG. 10V

| Appointment ID | Appointment Date | Age | Patient Name | Provider Name | Scheduled Estimate | YREG. | Last Contact | Next Contact |
|---|---|---|---|---|---|---|---|---|
| 868 | 06/03/2005 | 293 | | | $6,177.00 | | | |
| 843 | 07/11/2005 | 255 | | | $2,092.00 | | | |
| 8735 | 09/12/2005 | 192 | | | $4,015.00 | | | |
| 8737 | 09/12/2005 | 192 | | | $4,855.00 | | | |
| 1849 | 07/06/2005 | 260 | | | $8,707.00 | | | |
| 6053 | 10/07/2005 | 167 | | | $7,043.00 | | | |
| 830 | 07/11/2005 | 255 | | | $160.00 | | | |
| 9816 | 10/04/2005 | 170 | | | $1,041.00 | | | |
| 2559 | 07/07/2005 | 259 | | | $552.00 | | | |
| 10338 | 12/22/2005 | 91 | | | $2,816.00 | | | |
| 5348 | 08/18/2005 | 217 | | | $0.00 | | | |
| 8221 | 10/17/2005 | 157 | | | $2,774.00 | | | |
| 15160 | 11/16/2005 | 127 | | | $338.00 | | | |
| 8324 | 09/20/2005 | 184 | | | $2,395.00 | | | |
| 15721 | 12/05/2005 | 108 | | | $1,041.00 | | | |
| 5057 | 08/31/2005 | 204 | | | $9,405.00 | | | |
| 7802 | 01/23/2006 | 59 | | | $2,088.00 | | | |
| 2028 | 06/03/2005 | 293 | | | $8,050.00 | | | |
| 10680 | 09/19/2005 | 185 | | | $5,843.00 | | | |
| 1859 | 05/26/2005 | 301 | | | $160.00 | | | |
| 1222 | 06/29/2005 | 267 | | | $760.00 | | | |
| 8231 | 10/14/2005 | 160 | | | $2,774.00 | | | |
| 8161 | 10/21/2005 | 153 | | | $320.00 | | | |
| 799 | 05/03/2005 | 324 | | | $320.00 | | | |

METHOD AND SYSTEM FOR SCHEDULING TRACKING, ADJUDICATING APPOINTMENTS AND CLAIMS IN A HEALTH SERVICES ENVIRONMENT

BACKGROUND

Conventional systems and methods for processing claims in a health services environment do not readily detect errors and acts of fraud, particularly with respect to medical services that were not performed, incorrectly coded, coded against the wrong patient, etc. Typically, the scheduling of appointments, receiving of claims, and validating and payment of claims are performed by different specialized entities as disparate processes in a serial workflow, in which data is passed from one entity to another, often resulting in claims and payments being delayed or even lost. Furthermore, conventional claims processing systems and methods rely on validating received claims by manually checking for inconsistencies or other indicators that the claim is invalid, duplicative, in error, or fraudulent. This prior process is time consuming and prone to errors, resulting in received claims being substantially delayed in payment, not being paid correctly, or being paid without assurance as to whether the received claim is a valid claim.

SUMMARY

Methods and systems for scheduling, tracking, and adjudicating appointments and claims in a health services environment are presented.

An exemplary system for determining the appropriateness of service provider claims for payment includes a scheduling module configured to schedule appointments for patients with service providers based on requests for services, and generate appointment information corresponding to each of the scheduled appointments. The system further includes a claim intake module configured to receive claims from the service providers for payment of charges associated with services rendered by the service providers to the patients, and capture service information corresponding to each of the received claims. The system also includes an adjudication module configured to automatically identify candidate appointments that correspond to a particular received claim based on a degree of similarity between the service information associated with the particular received claim and the appointment information associated with the scheduled appointments. The adjudication module is further configured to present the particular received claim for payment when at least one of the candidate appointments corresponds to the particular received claim and flag the particular received claim for resolution when none of the candidate appointments corresponds to the particular received claim.

An exemplary method for determining the appropriateness of service provider claims for payment includes scheduling appointments for patients with service providers based on requests for services, generating appointment information corresponding to each of the scheduled appointments, and capturing service information corresponding to claims received from the service providers for payment of charges associated with services rendered by the service providers to the patients. The method further includes automatically identifying candidate appointments that correspond to a particular received claim based on a degree of similarity between the service information associated with the particular received claim and the appointment information associated with the scheduled appointments. Additionally, the method includes flagging the particular received claim for resolution when none of the candidate appointments corresponds to the particular received claim, and presenting the particular received claim for payment when at least one of the candidate appointments corresponds to the particular received claim.

Another exemplary system for determining the appropriateness of service provider claims for payment includes means for scheduling appointments for patients with service providers based on requests for services, means for generating appointment information corresponding to each of the scheduled appointments, and means for capturing service information corresponding to claims received from the service providers for payment of charges associated with services rendered by the service providers to the patients. The system further includes means for automatically identifying candidate appointments that correspond to a particular received claim based on a degree of similarity between the service information associated with the particular received claim and the appointment information associated with the scheduled appointments. Additionally, the system includes means for flagging the particular received claim for resolution when none of the candidate appointments corresponds to the particular received claim, and means for presenting the particular received claim for payment when at least one of the candidate appointments corresponds to the particular received claim.

BRIEF DESCRIPTION OF THE DRAWINGS

Other objects and advantages of the invention will become apparent to those skilled in the relevant art(s) upon reading the following detailed description of preferred embodiments, in conjunction with the accompanying drawings, in which like reference numerals have been used to designate like elements, and in which.

DETAILED DESCRIPTION

A detailed description of systems and methods for determining the appropriateness of service provider claims for payment is presented below. The explanation will be by way of exemplary embodiments to which the present invention is not limited.

By integrating the scheduling of appointments with service providers with the processing of claims from the service providers for services rendered, the systems and methods described herein may yield many advantages over systems and methods specializing in any one these aspects alone. By gathering information from inception to completion for any particular appointment, the systems and methods described herein are capable of rendering payment to the service providers in a more timely and accurate fashion. In particular, by generating information about each scheduled appointment, an approximate type and number of claims that should be received from service providers for each scheduled appointment can be estimated. In this way, a particular claim can be reviewed with greater accuracy when an appointment that corresponds to the claim is identified. The systems and methods described herein automatically match scheduled appointments to received claims with high speed and accuracy thereby reducing the risk of payment of erroneous, duplicate, or fraudulent claims. Furthermore, proper payment of all anticipated claims for a particular appointment can be better ensured using certain aspects of exemplary embodiments. For example, because the systems and methods described herein can automatically identify appointments for which no claims have been received, the service providers can be contacted and prompted to submit the outstanding claims. Thus, institutions are less likely to pay for the claims that they should not pay, and the service providers rendering the services are more likely to be paid for all of the claims for which they should be paid.

Process Overview

FIGS. 1-8 illustrate exemplary steps for a process 100 for determining the appropriateness of service provider claims for payment. Not all of the steps of FIG. 1 have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

First, in step 105, appointments for patients are scheduled with service providers based on requests for services. For example, when a client institution has a patient in need of health care services, the client institution securely forwards information about the patient and the desired appointment to a scheduler in the form of an electronic request.

Figure 1:
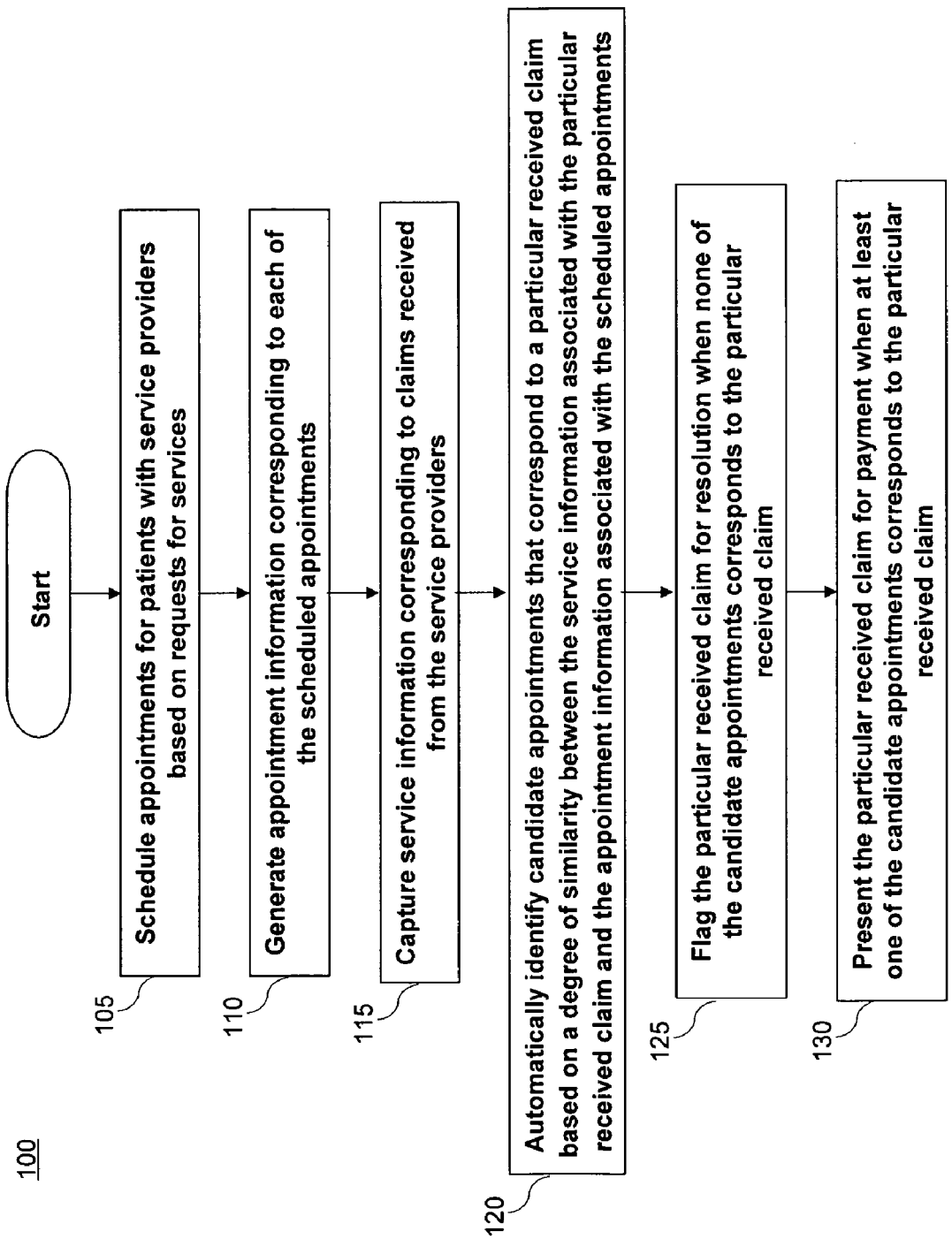
FIGS. 1-8 illustrate process flowcharts providing exemplary steps for determining the appropriateness of service provider claims for payment.
Figure 2:
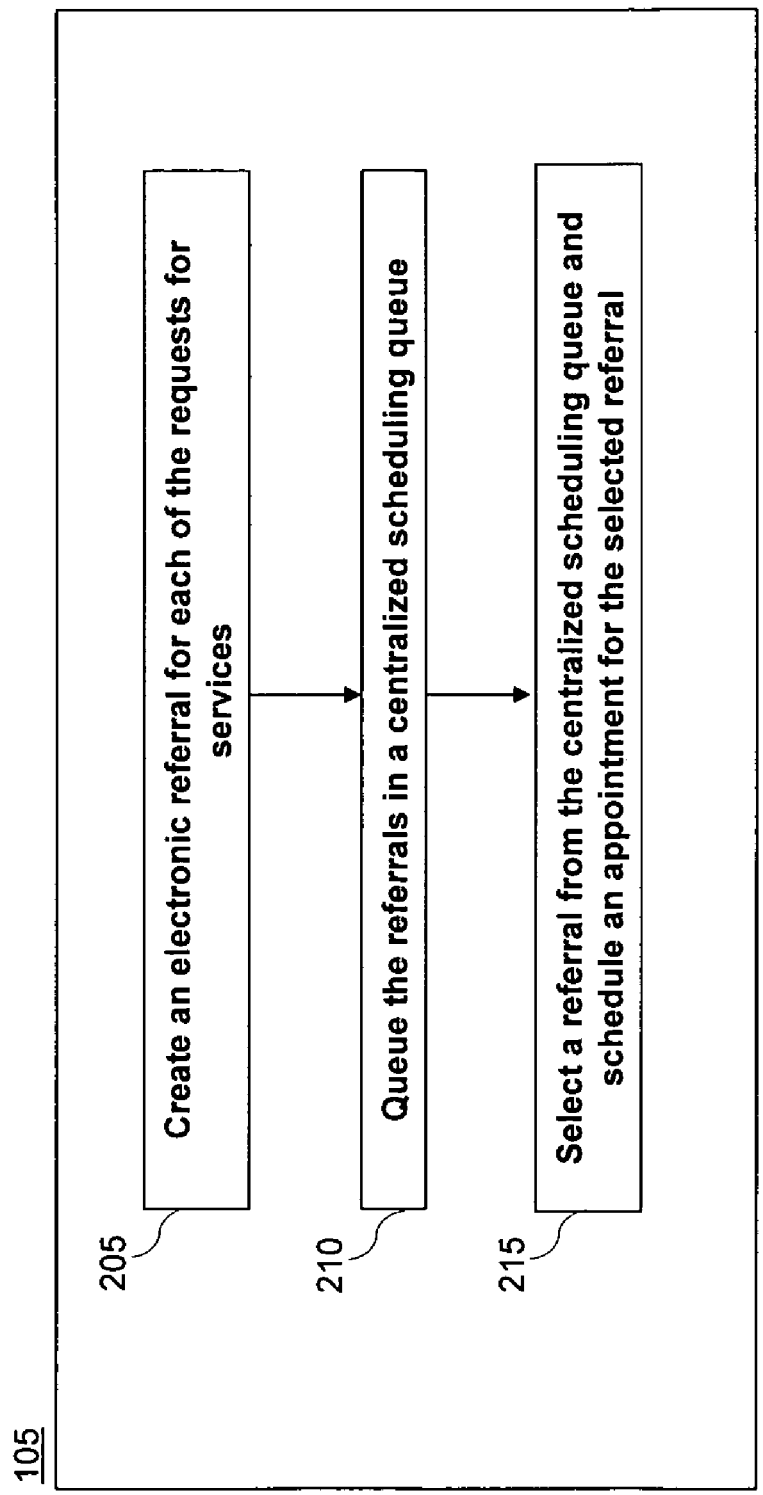

FIG. 2 illustrates detailed steps for executing step 105. In step 205, an electronic referral is created for each of the requests. While electronic referrals are preferred, they can be created in non-electronic format. Although, eventually the information from a non-electronic referral would likely be captured electronically, either in the form of an image of the non-electronic referral or, in other circumstances, the information would be keyed in from the non-electronic referral. As will be described in more detail below with respect to the detailed description of the exemplary implementation, each electronic referral includes the patient and desired appointment information supplied by the client institution, in addition to contact information for the client institution (usually for the contract manager) and for the primary scheduler. It may also capture the reasons for the referral, the types of services expected to be rendered (e.g., blood tests), or the circumstances for the referral (e.g., the patient has a medical condition such as diabetes). This referral may be generated by a doctor or clinician or, in some circumstances, by the patient (e.g., preferred provider organizations (PPOs)).

Each electronic referral is assigned a unique referral identification code and, in step 210, the referrals are queued in a centralized scheduling queue of a scheduling module. In step 215, a scheduler selects a referral from the centralized scheduling queue and schedules an appointment for the selected referral. In most instances, the scheduler is a person. Additionally, in most cases, the scheduler will schedule the appointment with a service provider(s) identified in a particular network of service providers associated with the client institution. Typically, the scheduler will schedule the appointment by telephoning or otherwise communicating directly with the service provider. In the event that there is no provider in the network for a particular requested service, the scheduler can attempt to recruit a service provider in the required specialty and negotiate a single-patient agreement for the appointment. When scheduling an appointment, the scheduler may take into consideration any predefined scheduling rules for the client institution and/or service provider (e.g., a scheduling rule for a correctional institution might specify that only one maximum security inmate patient can be at an off-site appointment at a time).

Figure 3:
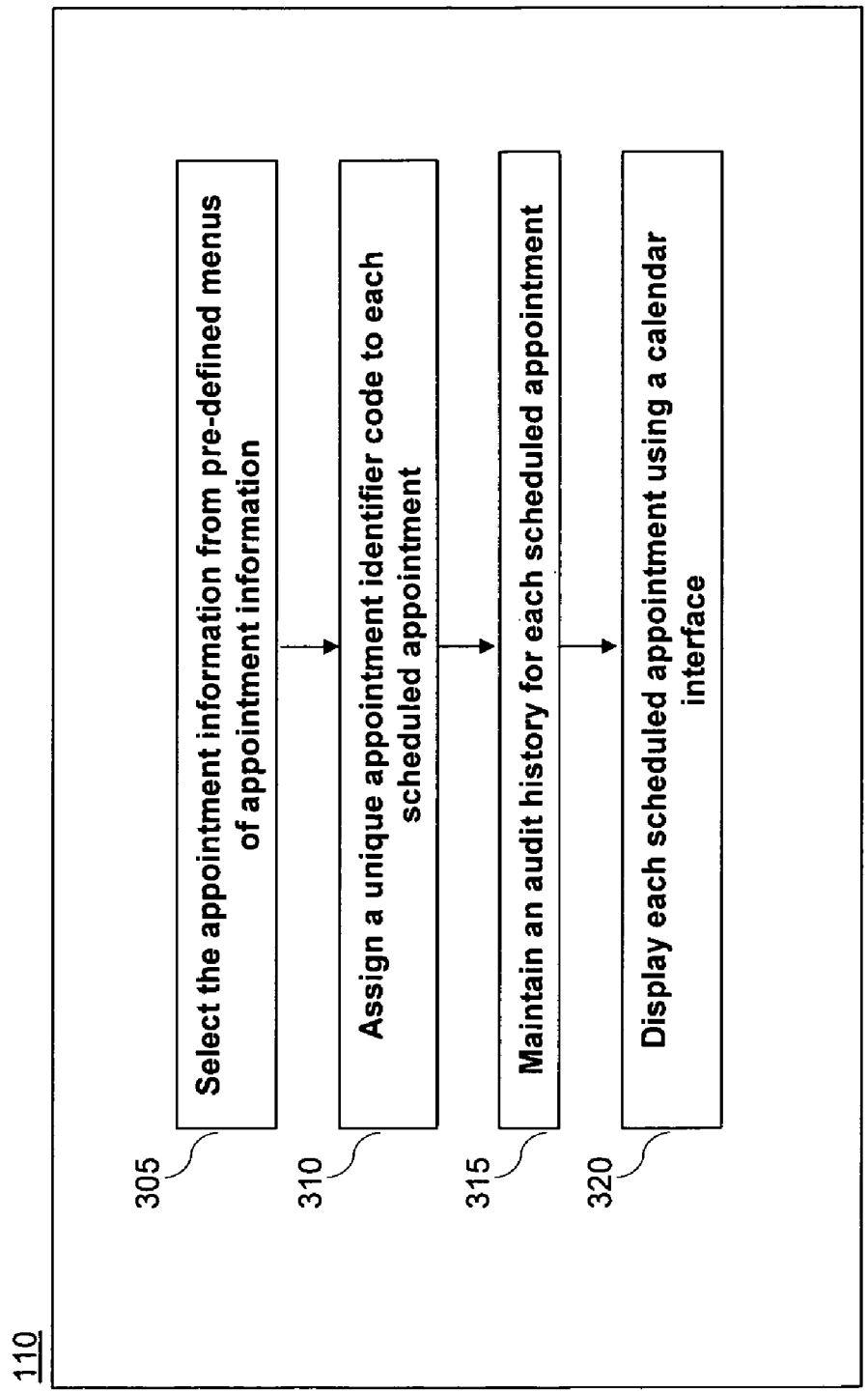

Next, in step 110, appointment information corresponding to each of the scheduled appointments is generated. FIG. 3 illustrates detailed steps for executing step 110. As will be described in more detail below with respect to the detailed description of the exemplary implementation, in step 305, the scheduler (or other user) views an electronic referral and can select corresponding appointment information from predefined menus of appointment information (e.g., service provider, appointment date, appointment time, etc.). In one embodiment, the scheduler/user selects a unique service identifier code for each requested service that can be used a cross-check against Medicare-defined service codes to validate received claims in subsequent steps. Some appointment information may be manually keyed in by the scheduler/user, in which case a double-blind entry process can be implemented to detect and correct keying errors. The double-blind entry process entails two data entry people entering the same information, but "blind" to each other. Discrepancies are then identified and resolved, usually by a third person, particularly when the discrepancy is not automatically resolvable through spell-checker or grammar-checker software components. Additionally, the scheduler/user can use the scheduling module to attach associated information files (e.g., x-ray films) as appointment information.

In step 310, a unique appointment identifier code can be assigned to each of the scheduled appointments that can be used to link appointments with received claims in subsequent steps. Advantageously, in step 315, an audit history can be maintained for each of the scheduled appointments to track when each appointment was created, modified, canceled, etc. In step 320, each scheduled appointment can be displayed using a calendar interface such that a user (e.g., the client institution, the scheduler, the service provider, etc.) can select a displayed scheduled appointment to access corresponding appointment information, perhaps each user potentially having different access rights to different types of appointment information.

Figure 4:
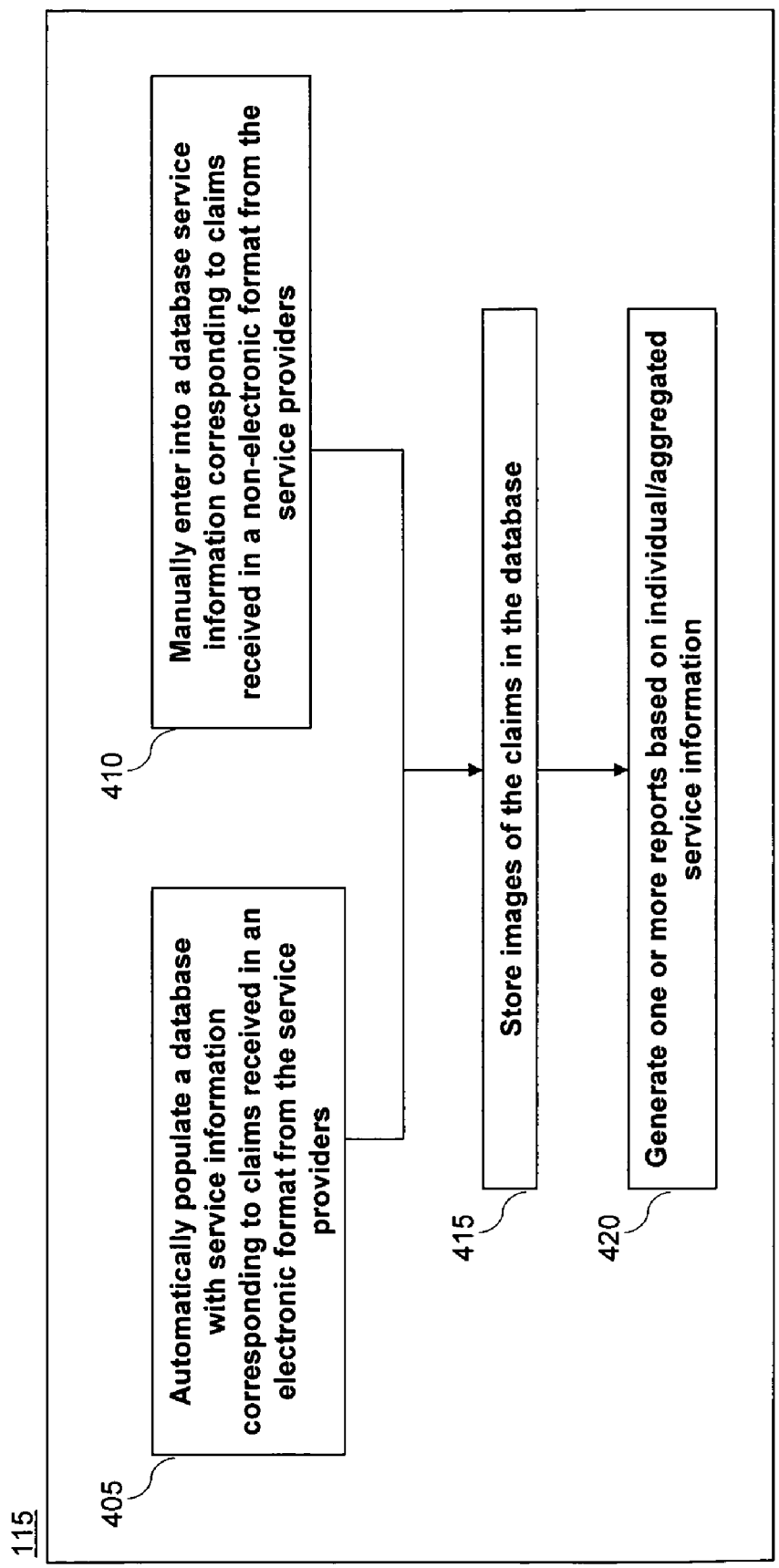

In step 115, service information is captured that corresponds to claims received from the service providers for payment of charges associated with services rendered by the service providers to the patients. FIG. 4 illustrates detailed steps for executing step 115. In step 405, a service information database may be automatically populated with service information corresponding to claims received in an electronic format from the service providers. In step 410, the database may be manually populated with service information corresponding to claims received in a non-electronic format from the service providers. In this latter case, the service information can be keyed into the database in accordance with the double-blind entry process described above to detect and correct keying errors. In step 415, images of the claims can be stored in the database. Claims received in non-electronic format can be scanned to generate the claim images.

Optionally, in step 420, one or more reports can be generated based on individual or aggregated service and/or appointment information, such as predefined institution-specific reports, financial reports, contract reports, and utilization reports. In an embodiment, step 420 includes ad hoc report generation. In another embodiment, step 420 includes generating a pricing service sheet that identifies a pricing structure for a particular network of service providers.

Figure 5:
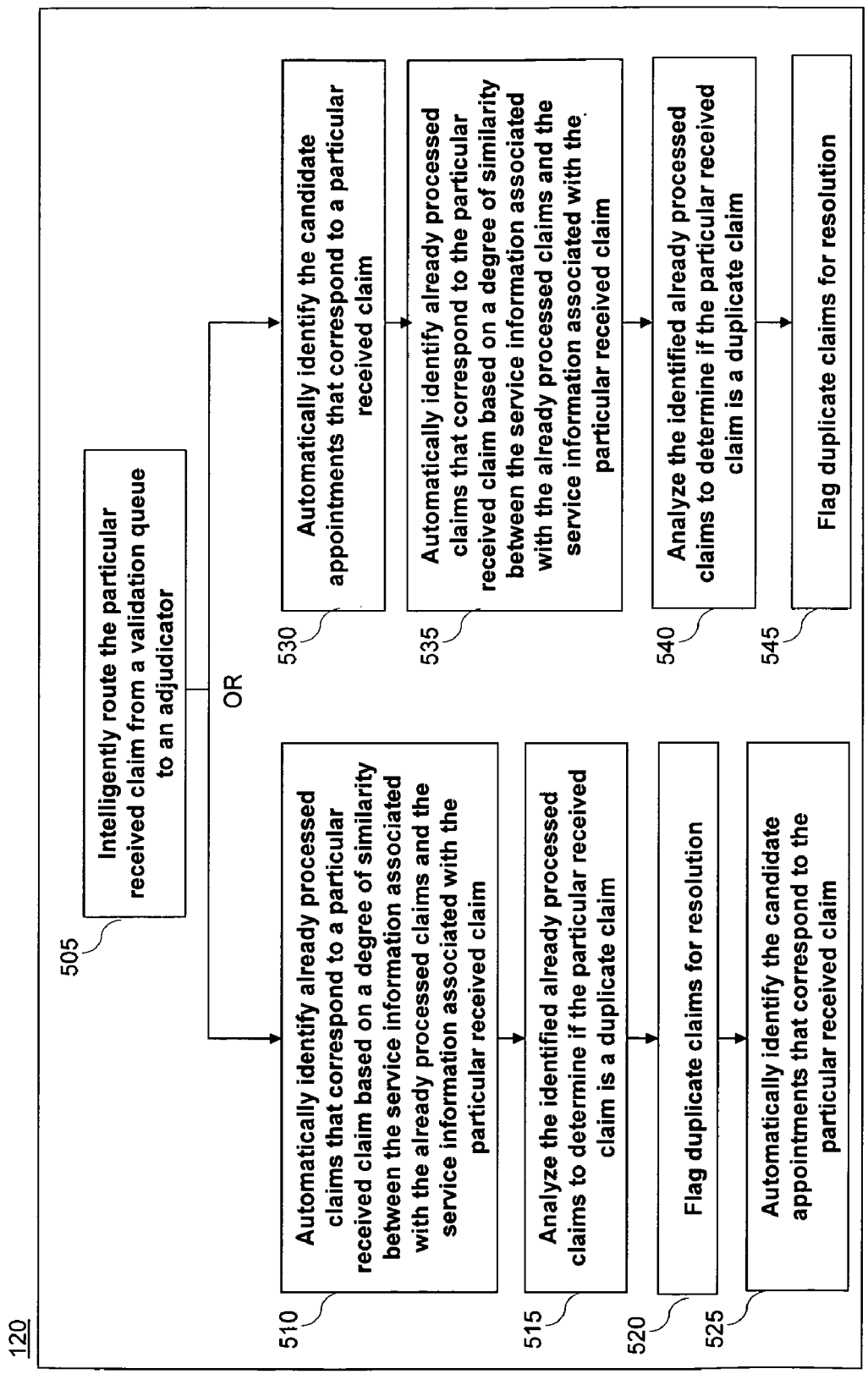

In step 120, the process 100 further includes automatically identifying, using logic, fuzzy logic and/or artificial intelligence (AI), candidate appointments that correspond to a particular received claim based on a degree of similarity between the service information associated with the particular received claim and the appointment information associated with the scheduled appointments. Any suitable logic, fuzzy logic, or AI system could be used and would likely be centrally optimized for circumstances, particularly if the circumstances are dynamic. FIG. 5 illustrates detailed steps for executing step 120. In step 505, the particular received claim is intelligently routed from an adjudication queue of received claims to an adjudicator. In an embodiment, the particular received claim is routed to an initial adjudicator that is determined to be available, and if the initial adjudicator does not respond within a predetermined period of time, the particular received claim is routed to another available adjudicator so that the received claims do not lag in the adjudication queue.

Next, either steps 510-525 are performed or steps 530-545 are performed. In the first case, a duplicate check is performed in steps 510-520 before an appointment match is performed in step 525. In particular, in step 510, already processed claims that correspond to a particular received claim are automatically identified using logic, fuzzy logic and/or AI based on a degree of similarity between the service information associated with the already processed claims and the service information associated with the particular received claim. In step 515, the identified already processed claims are analyzed to determine if the particular received claim is a duplicate of any of the identified already processed claims. In an embodiment, step 515 includes having the adjudicator analyze the identified already processed claims to determine if the service provider submitted a duplicate claim. In another embodiment, step 515 includes automatically determining if the service provider submitted a duplicate claim. In step 520, duplicate claims are flagged for resolution.

Alternatively, in the latter case, after an appointment match is performed in step 530, a duplicate match is performed in steps 535-545. In particular, in step 535, already processed claims that correspond to a particular received claim are automatically identified using logic, fuzzy logic and/or AI based on a degree of similarity between the service information associated with the already processed claims and the service information associated with the particular received claim. In step 540, the identified already processed claims are analyzed to determine if the particular received claim is a duplicate claim. In an embodiment, step 540 includes having the adjudicator analyze the identified already processed claims to determine if the service provider submitted a duplicate claim. In another embodiment, step 540 includes automatically determining if the service provider submitted a duplicate claim. In step 545, duplicate claims are flagged for resolution.

In an embodiment, steps 525 and 530 include displaying the candidate appointments for review by an adjudicator. The adjudicator can then determine whether to flag the particular received claim for resolution or to present the particular received claim for payment. In another embodiment, steps 525 and 530 include only displaying for review by an adjudicator candidate appointments that do not directly correspond to the particular received claim. In this case, candidate appointments that directly correspond to the particular received claim may not be displayed for review by the adjudicator to further expedite the validation process.

Figure 6:
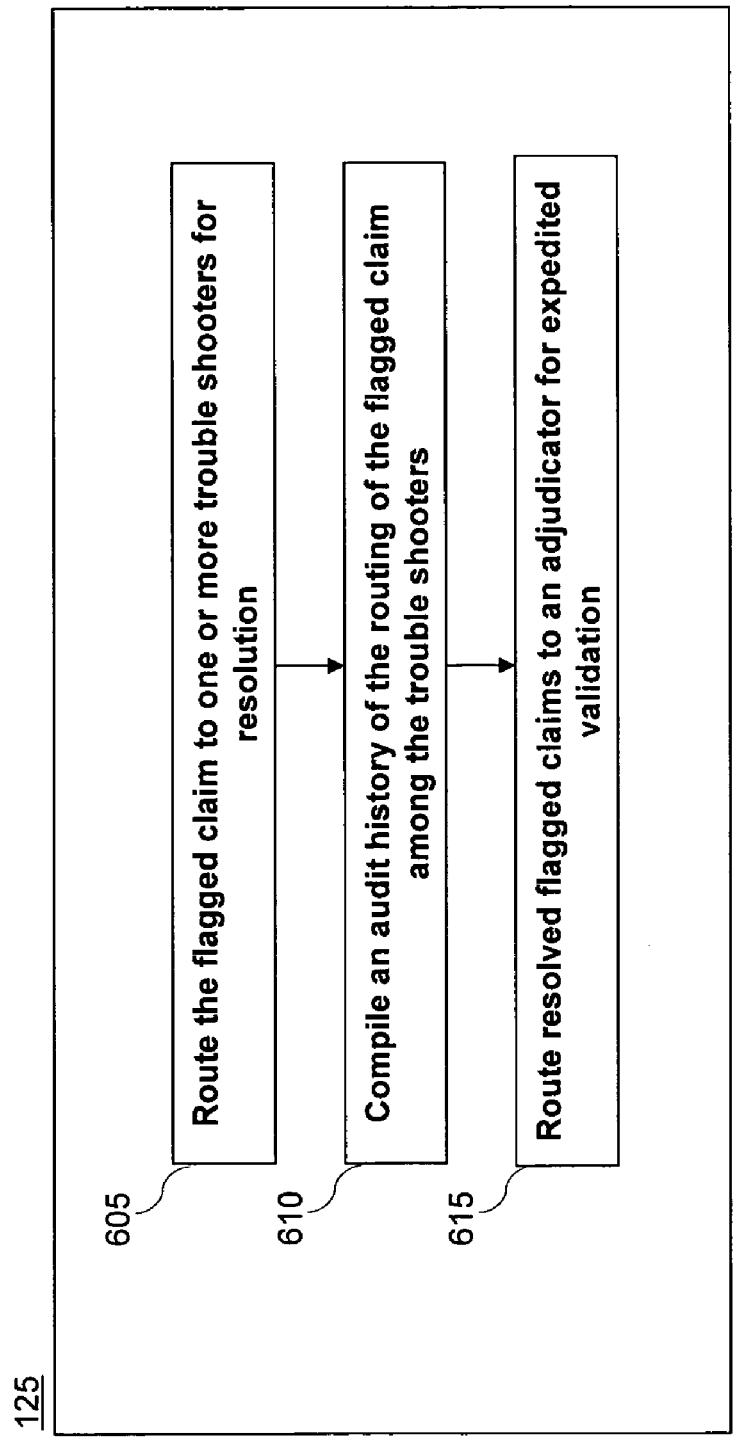

In step 125 of the process 100, the particular received claim is flagged for resolution when none of the candidate appointments corresponds to the particular received claim. FIG. 6 illustrates detailed steps for executing step 125. In step 605, the flagged claim is routed to one or more trouble shooters for resolution (e.g., to the contract manager for pricing problems, to the service provider for duplicate claims, etc.). This process of routing flagged claims among trouble shooters is described in more detail below with respect to the detailed description of the exemplary implementation. Essentially, instead of flagged claims lagging in the adjudication queue, the flagged claim is advantageously routed among various trouble shooters to address the problem with the flagged claim, or at least to identify where resolution has been stymied. In step 610, an audit history of the routing of the flagged claim among the trouble shooters is compiled. Compiling an audit history can be advantageous for motivating faster resolution by the trouble shooters of the problem associated with the flagged claim. In step 615, resolved flagged claims are routed to an adjudicator for expedited validation. In one embodiment, the resolved claims can be routed to the top of the adjudication queue so that they are adjudicated as quickly as possible following resolution.

Figure 7:
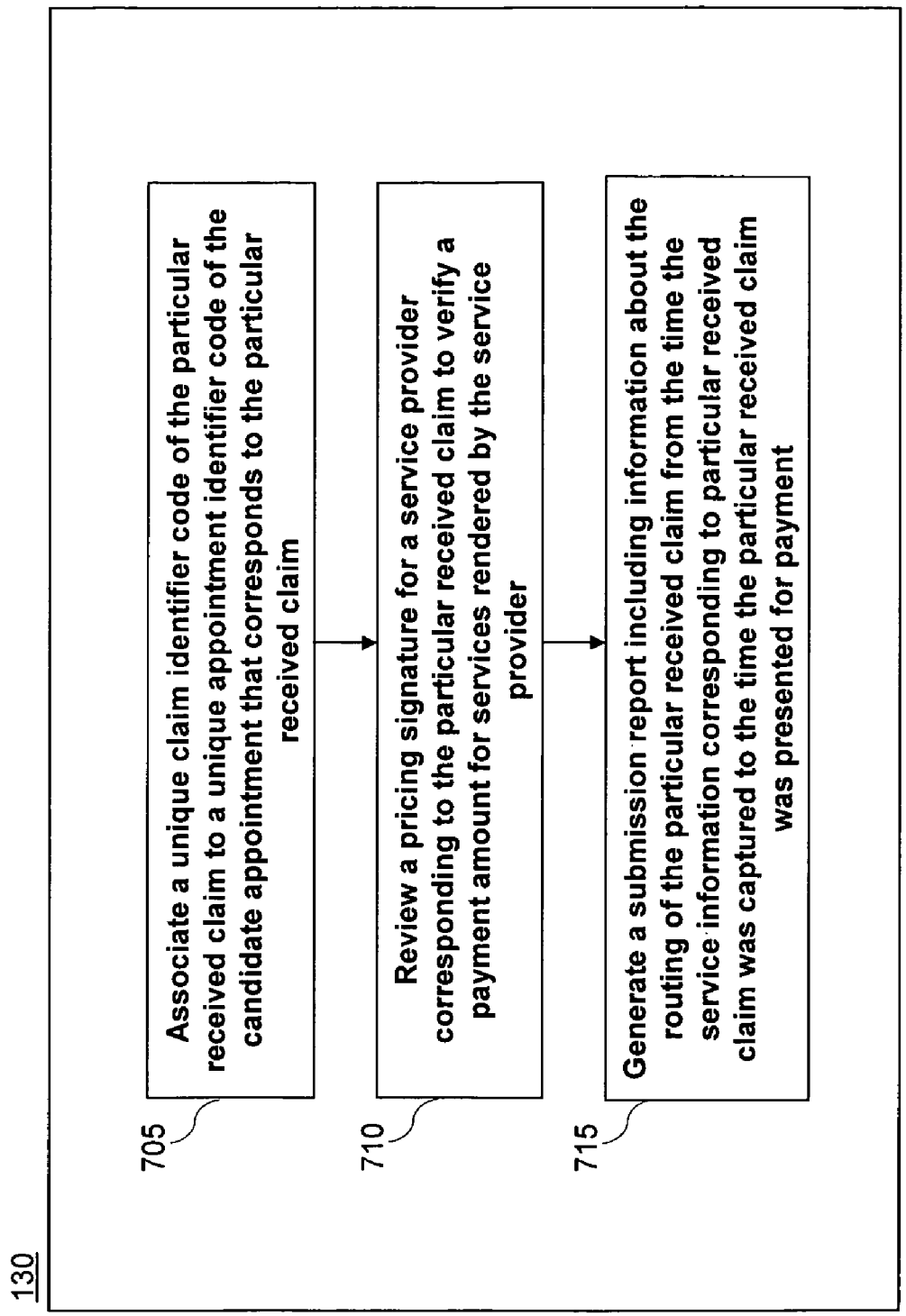

In step 130, the particular received claim is presented for payment when at least one of the candidate appointments corresponds to the particular received claim. FIG. 7 illustrates detailed steps for executing step 130. In step 705, a unique claim identifier code of the particular received claim can be associated with a unique appointment identifier code of the candidate appointment that corresponds to the particular received claim. In this way, the candidate appointment and its associated appointment information can be electronically linked to the particular received claim and its corresponding service information. In step 710, a pricing signature for a service provider corresponding to the particular received claim can be reviewed to verify a payment amount for services rendered by the service provider. The "pricing signature" refers to unique information associated with the service provider that assists in verifying the correct pricing. In step 715, a submission report can be generated that includes information about the routing of the particular received claim from the time the service information corresponding to particular received claim was captured to the time the particular received claim was presented for payment. The submission report can then be forwarded to the client institution. In an embodiment, the submission report is electronically forwarded to the client institution and includes selectable links to related appointment and/or service information.

In an embodiment, steps 125 and 130 include automatically flagging the particular received claim for resolution when none of the candidate appointments corresponds to the particular received claim, and automatically presenting the particular received claim for payment when at least one of the candidate appointments corresponds to the particular received claim, respectively, to expedite the validation process.

Figure 8:
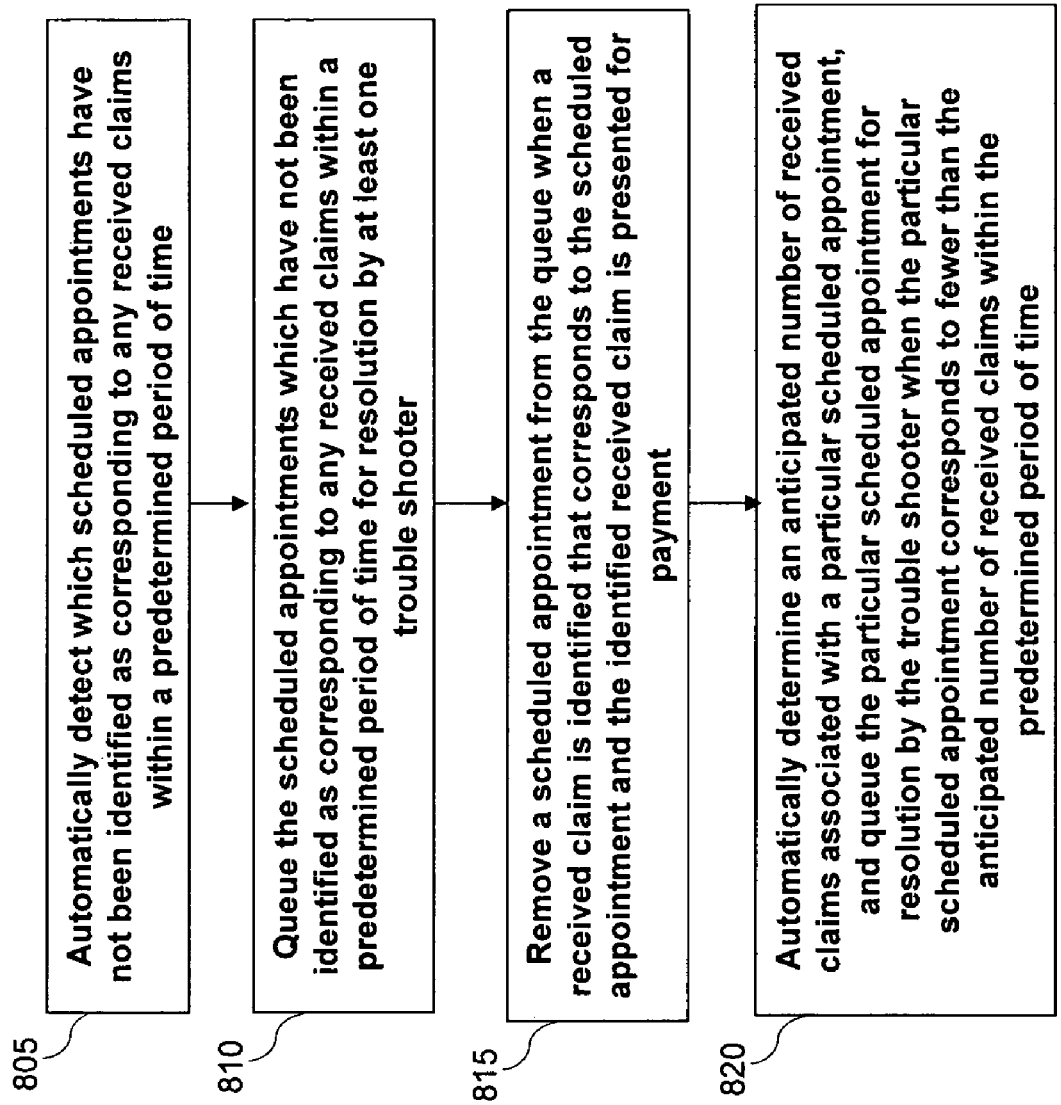

Optionally, the process 100 depicted in FIGS. 1-7 includes the additional steps shown in FIG. 8. In step 805, scheduled appointments that have not been identified as corresponding to any received claims within a predetermined period of time can be automatically detected. In step 810, the scheduled appointments which have not been identified as corresponding to any received claims within a predetermined period of time can be queued for resolution by at least one trouble shooter. The trouble shooter can then contact the service provider(s) associated with the scheduled appointment and request that a claim be submitted for payment. In step 815, a scheduled appointment is removed from the queue when a received claim is identified that corresponds to the scheduled appointment and the identified received claim is presented for payment. In this way, the service providers are more likely to receive payment for all of the claims they are entitled to. Furthermore, if the service providers are promptly paid, they are more likely to contract with the client institutions to provide health care services.

In step 820, an anticipated number of received claims associated with a particular scheduled appointment can be automatically determined, and the particular scheduled appointment can be queued for resolution by the trouble shooter when the particular scheduled appointment corresponds to fewer than the anticipated number of received claims within the predetermined period of time. In this way, the particular scheduled appointment can be analyzed on a procedure or service basis to estimate how many claims are anticipated to be received from the service providers after the appointment occurs. When fewer than the anticipated number of claims is received within a predetermined period after the appointment occurs, the trouble shooter can contact the applicable service provider(s) and request that the missing claims be submitted for payment.

System Overview

Figure 9:
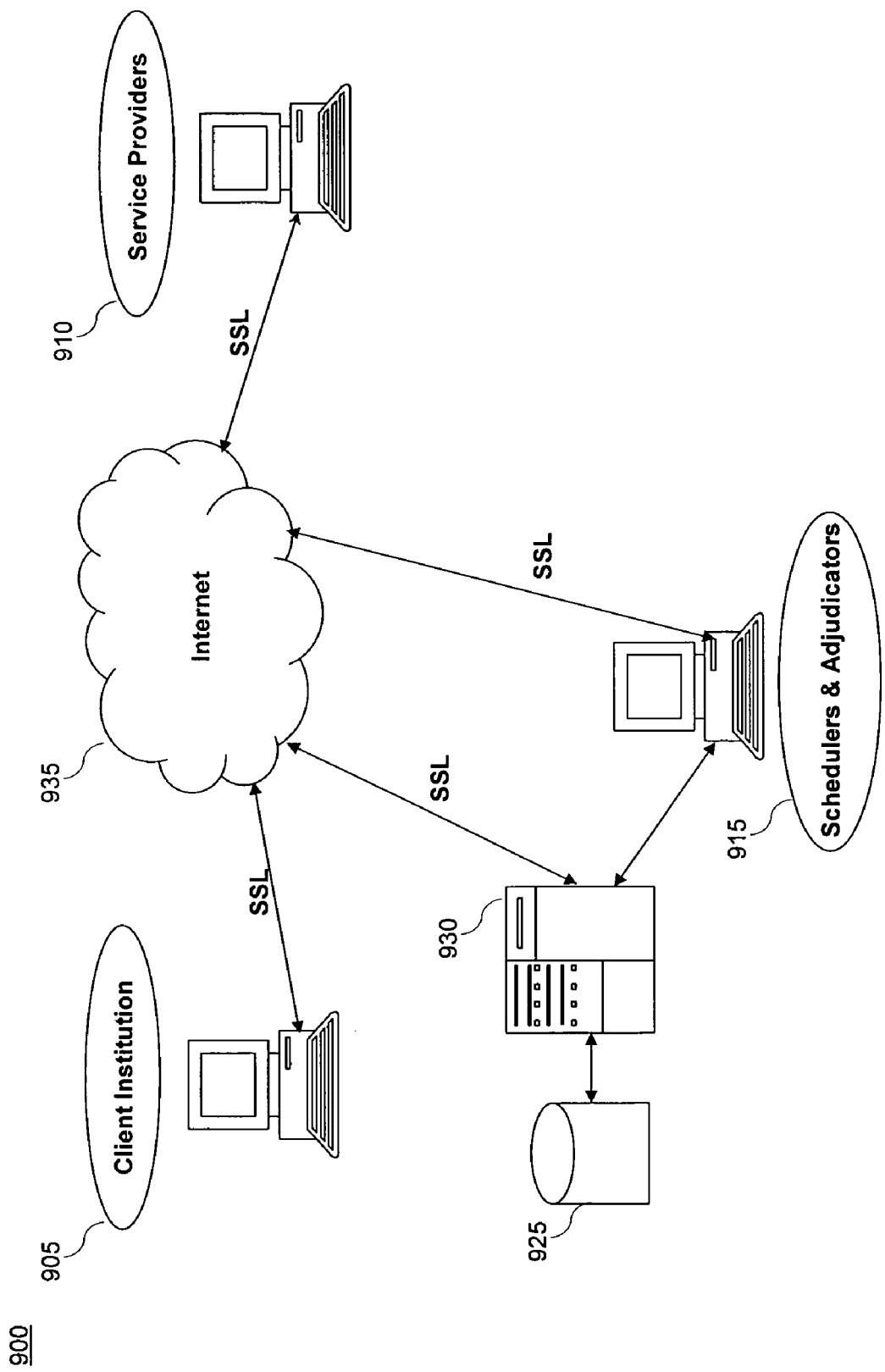
FIG. 9 illustrates a exemplary high-level network for implementing a system for determining the appropriateness of service provider claims for payment.

FIG. 9 illustrates an exemplary high-level network 900 for implementing a system for determining the appropriateness of service provider claims for payment. As shown in FIG. 9, the system can be employed in conjunction with a computer-based system, where the elements can be implemented in hardware, software, firmware, or combinations thereof. Network 900 includes client institution workstations 905, service provider workstations 910, and scheduler and adjudicator workstations 915. Each of the workstations is configured to communicate with an application server 930 via Secure Sockets Layer (SSL) internet connections 935. As shown in FIG. 9, the schedulers and adjudicators 915 can also access application server 930 via a secure closed network connection.

The server 930 includes processors and memory for hosting different modules, which are described in more detail below with respect to the detailed description of the exemplary implementation. Briefly, the system for determining the appropriateness of service provider claims for payment includes a scheduling module configured to schedule appointments for patients with the service providers 910 based on requests for services from the client institution 905, and generate appointment information corresponding to each of the scheduled appointments. The appointment information can be stored in a database 925.

The system further includes a claim intake module configured to receive claims from the service providers 910 for payment of charges associated with services rendered by the service providers 910 to the patients and capture service information corresponding to each of the received claims. The service information can also be stored in database 925.

The system also includes an adjudication module configured to automatically identify candidate appointments that correspond to a particular received claim based on a degree of similarity between the service information associated with the particular received claim and the appointment information associated with the scheduled appointments. The adjudication module is further configured to present the particular received claim for payment when at least one of the candidate appointments corresponds to the particular received claim and flag the particular received claim for resolution when none of the candidate appointments corresponds to the particular received claim.

Detailed Description of Exemplary Implementation

Figure 10A:
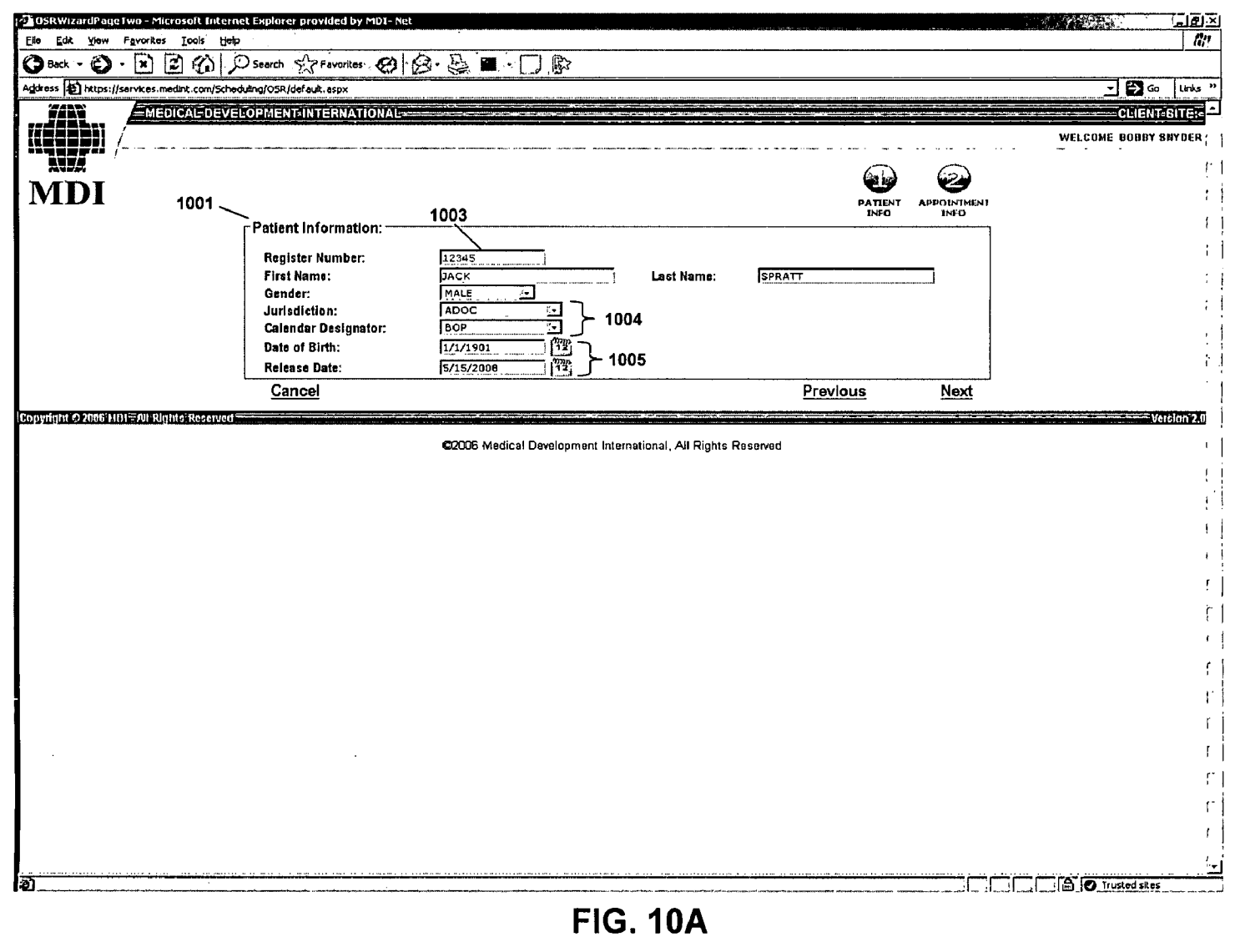
Figure 10B:
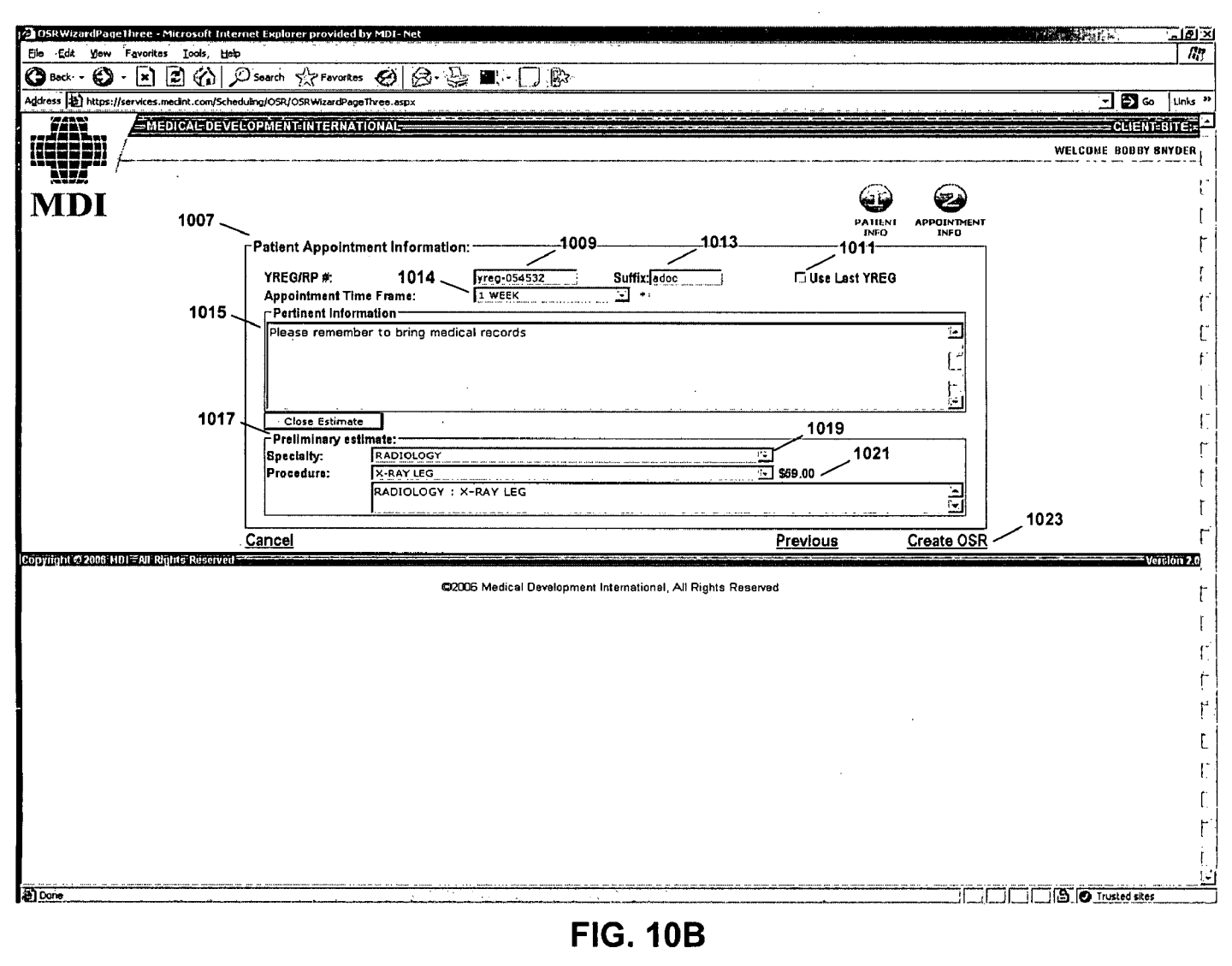
Figure 10C:
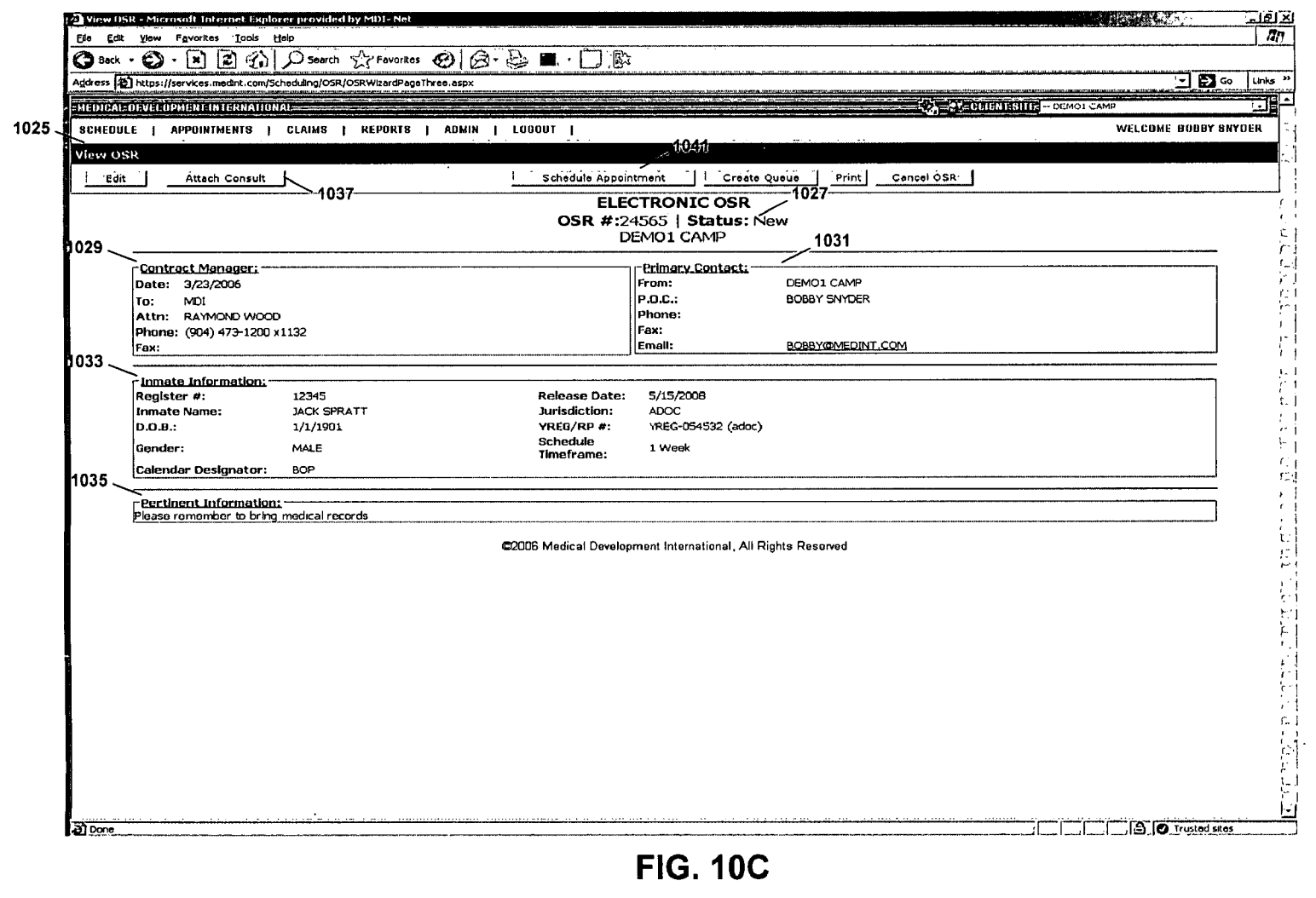
Figure 10D:
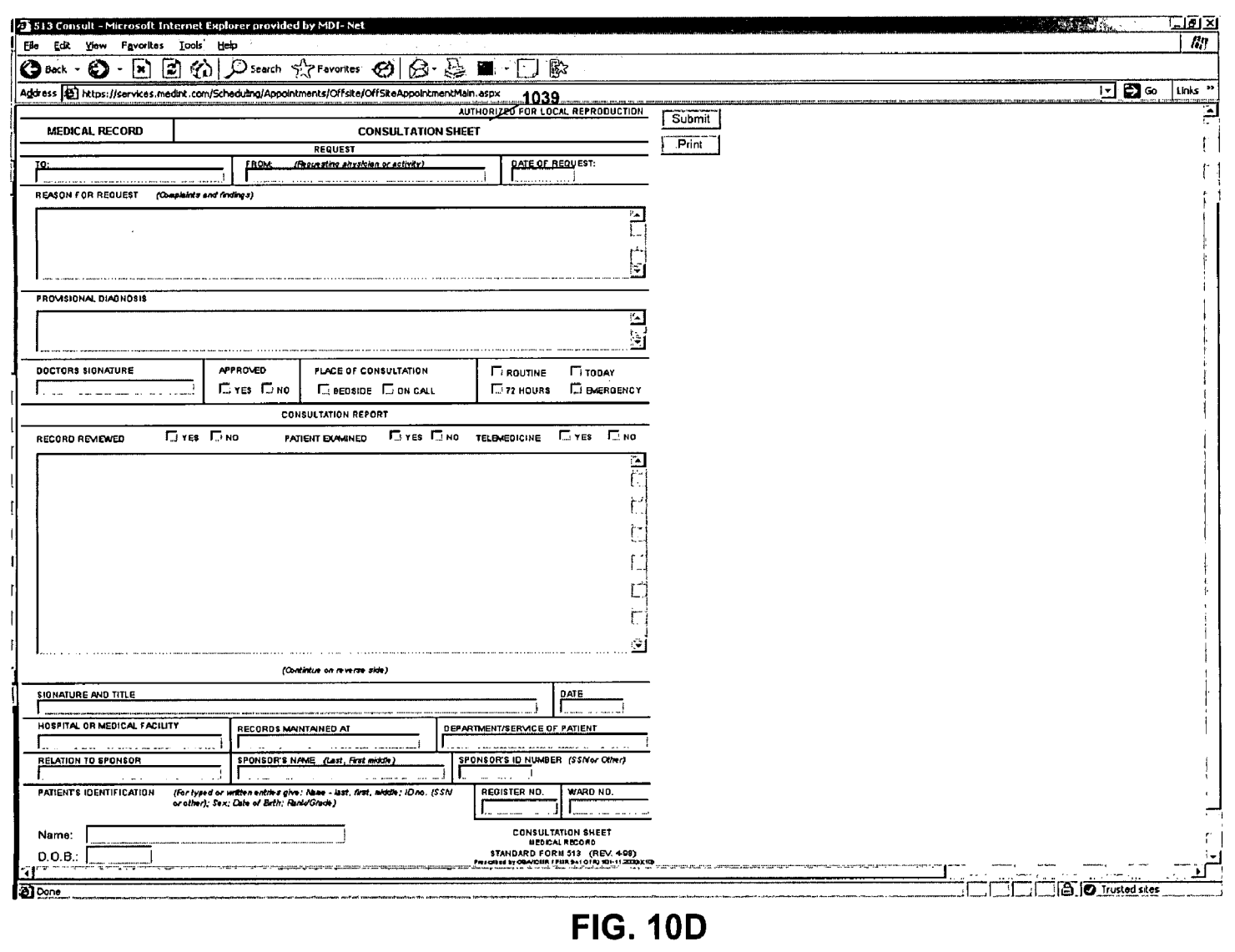

FIGS. 10A-10X illustrate an exemplary implementation of the systems and methods described herein for determining the appropriateness of service provider claims for payment in the context of providing health care services to inmate patients in a correctional institution. Persons of skill in the relevant art(s) will understand that the systems and methods described herein need not be limited to the application of providing health care services to inmate patients in a correctional institution, and can be applicable to providing health care services in other environments, in which control over patient access to the health care services can be exercised (e.g., school campuses, health maintenance originations (HMOs), military bases, psychiatric institutions, rehabilitation facilities, etc.). PPOs could also benefit by letting members log-on to a scheduling module for "self-referrals" at step 105 of FIG. 1, for instance. Such institutions are referred to herein as "clients" and "client institutions." Additionally, persons of skill in the relevant art(s) will understand that the systems and methods described herein need not be limited to health care services and providers (e.g., hospitals, doctors, dentists, physicians assistants, therapists, nurse practitioners, etc.), but could possibly be implemented in other service environments, as well.

Web-Based Scheduling Tool

Figure 10E:
FIGS. 10A-10X illustrate screen captures of an exemplary implementation of the systems and methods described herein for determining the appropriateness of service provider claims for payment, in the context of providing health care services to inmate patients in a correctional institution.
Figure 10F:
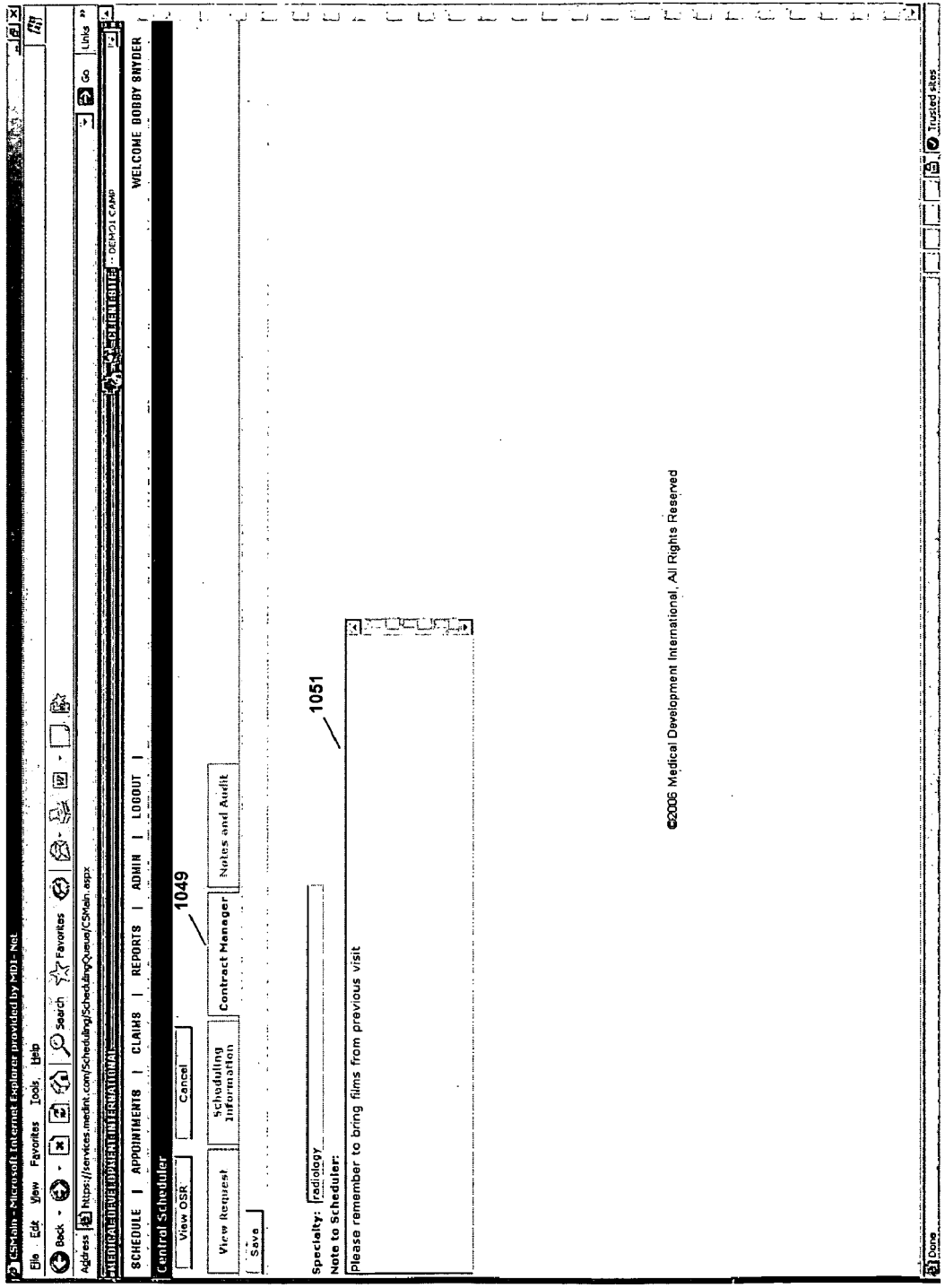
Figure 10G:
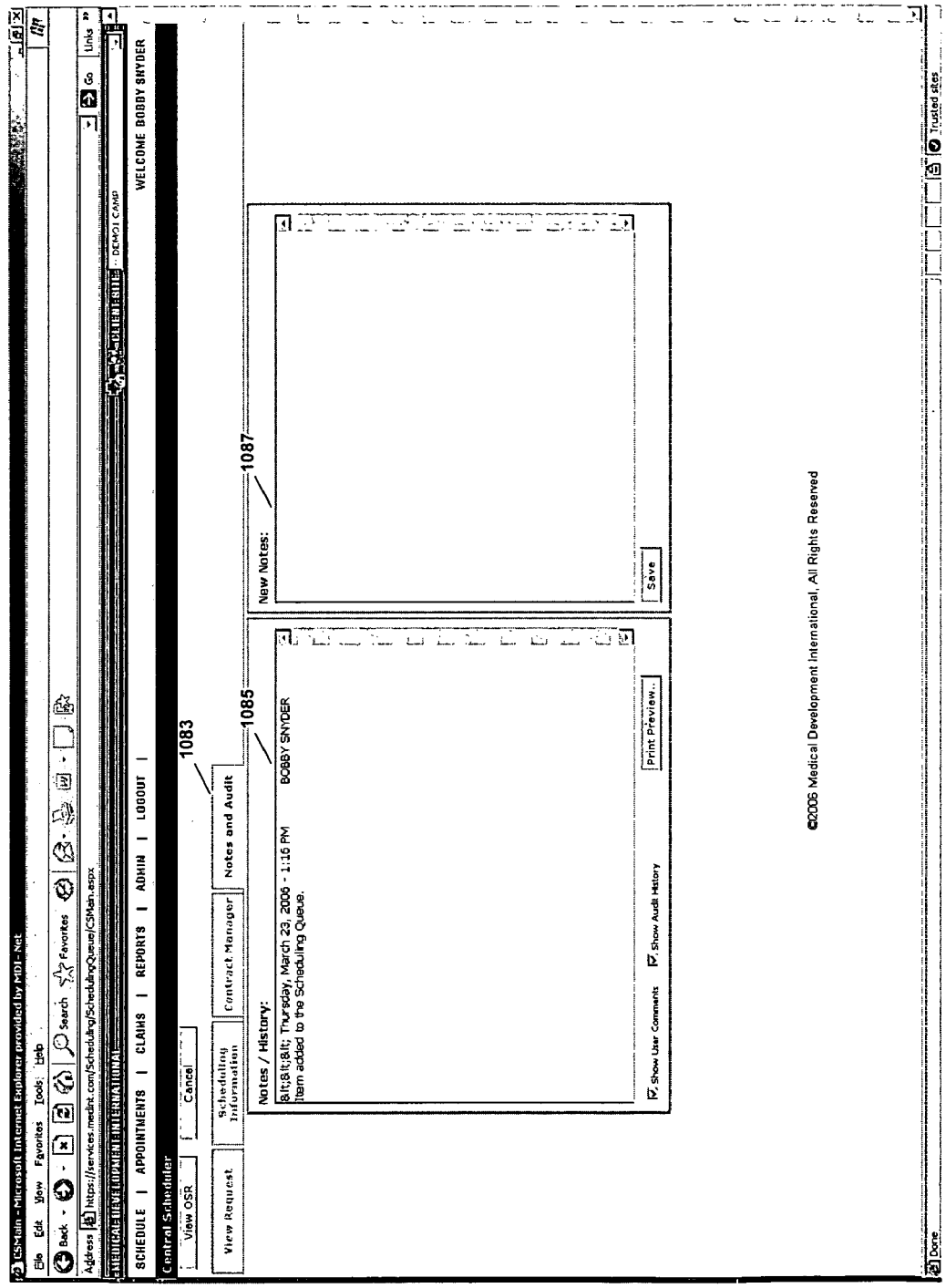
Figure 10H:
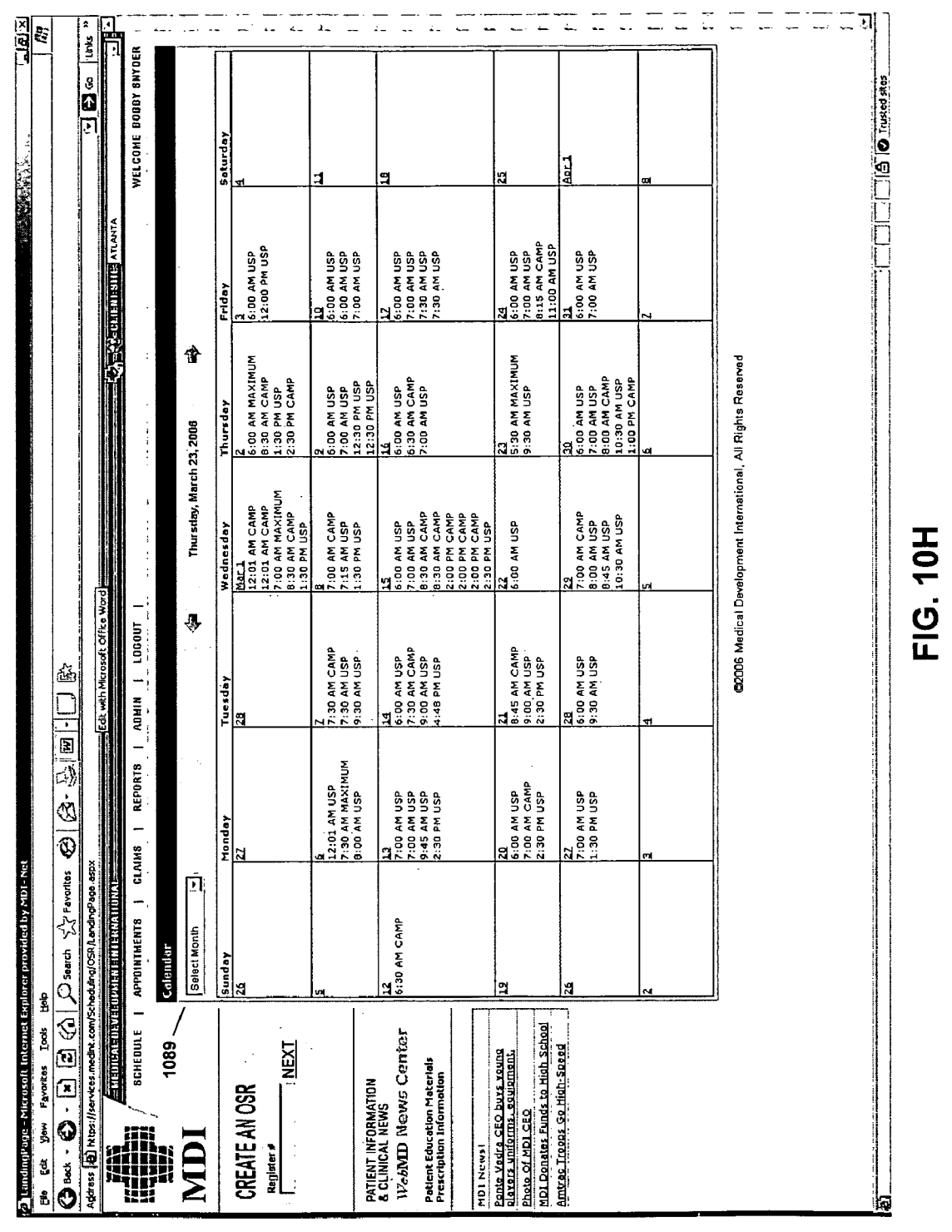
Figure 10I:
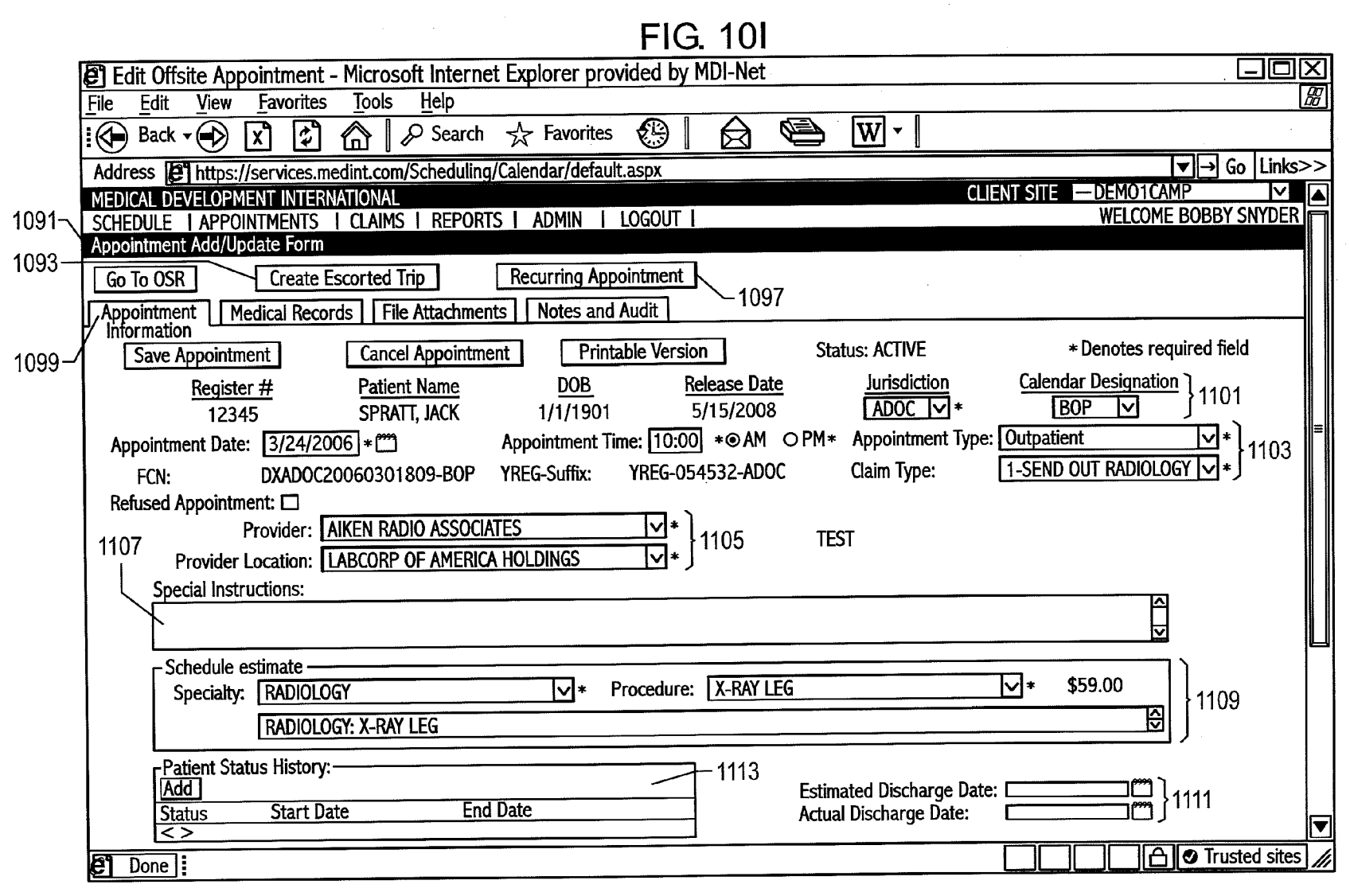
Figure 10J:
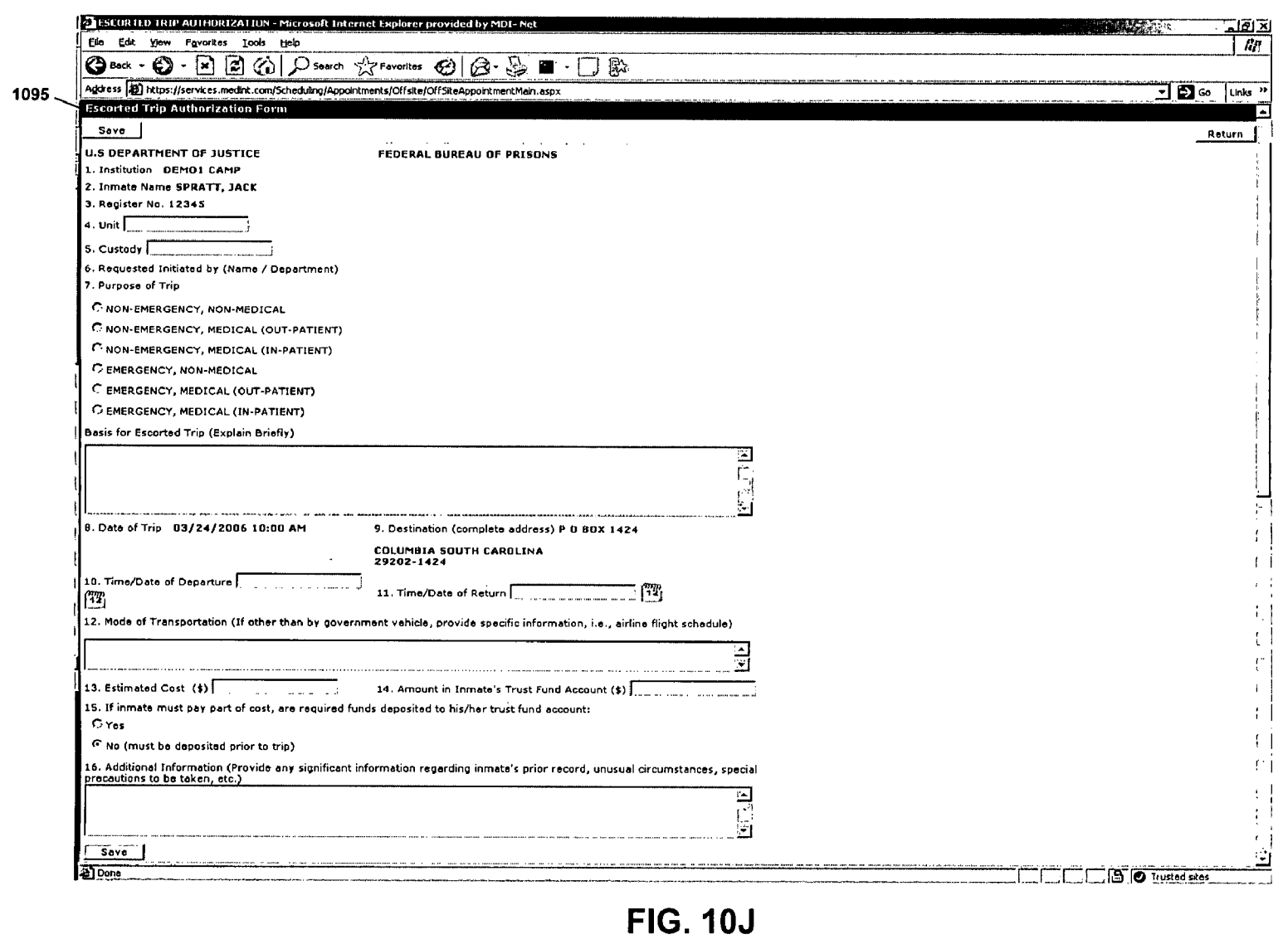
Figure 10K:
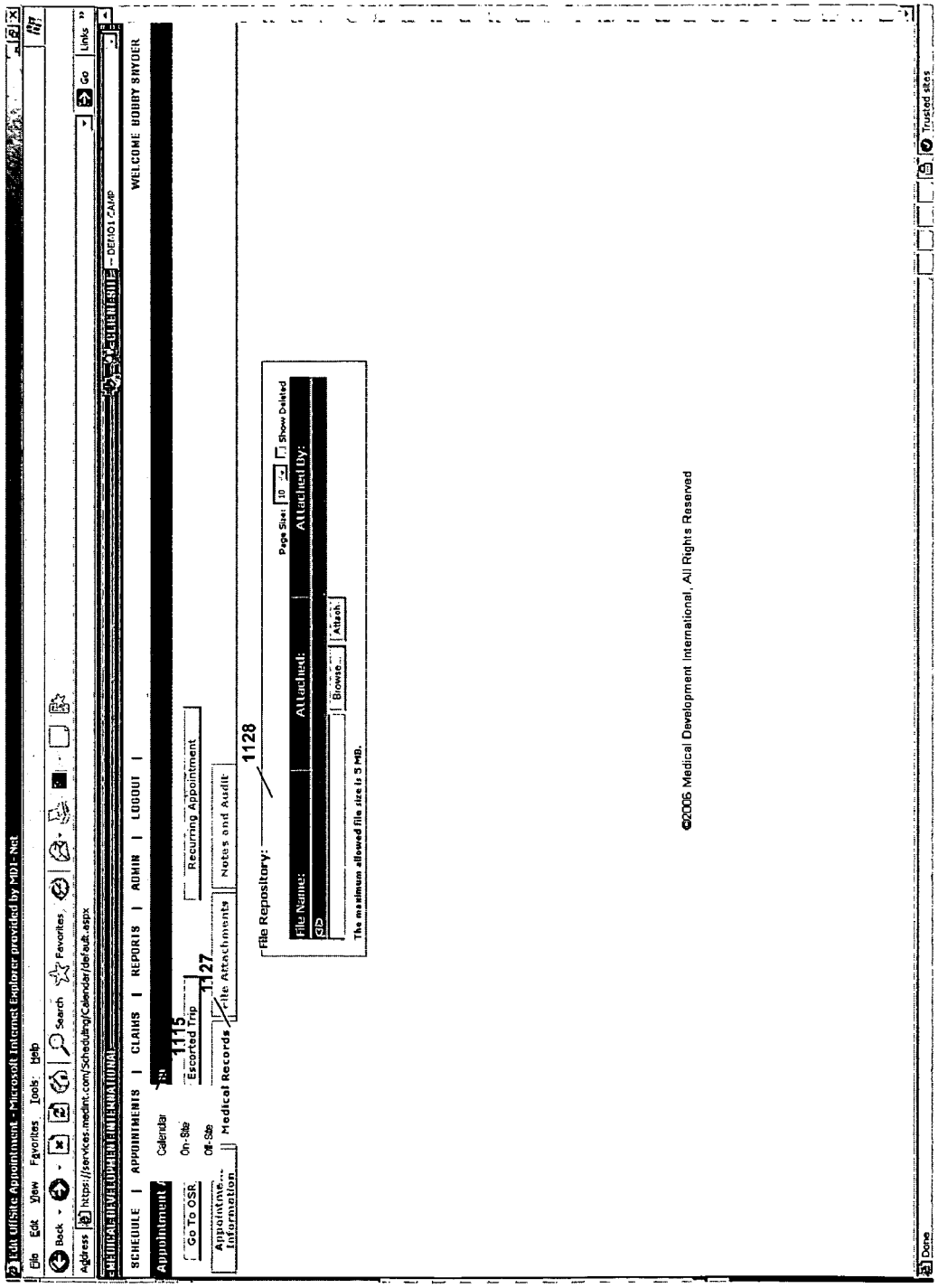
Figure 10L:
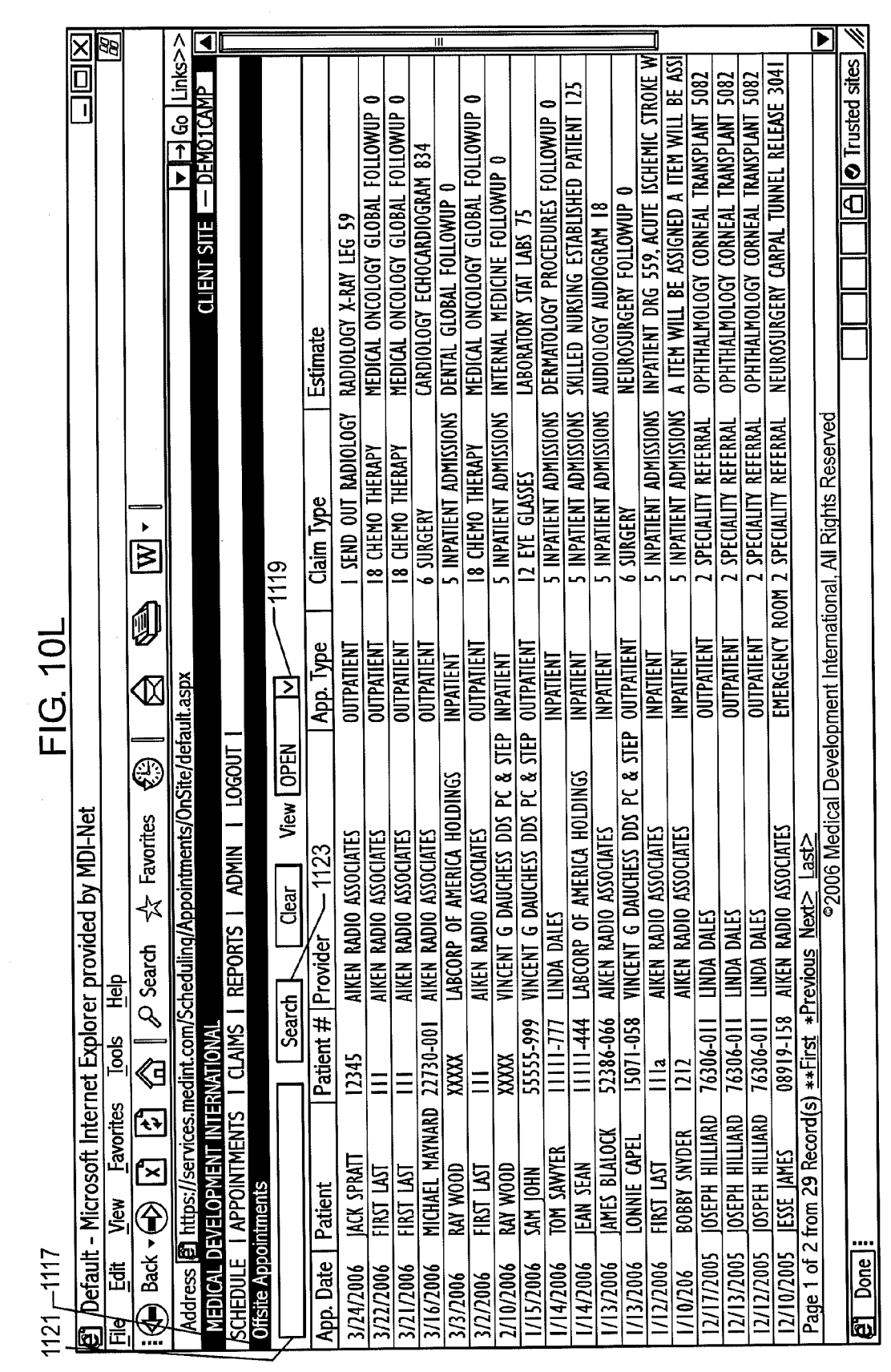
Figure 10M:
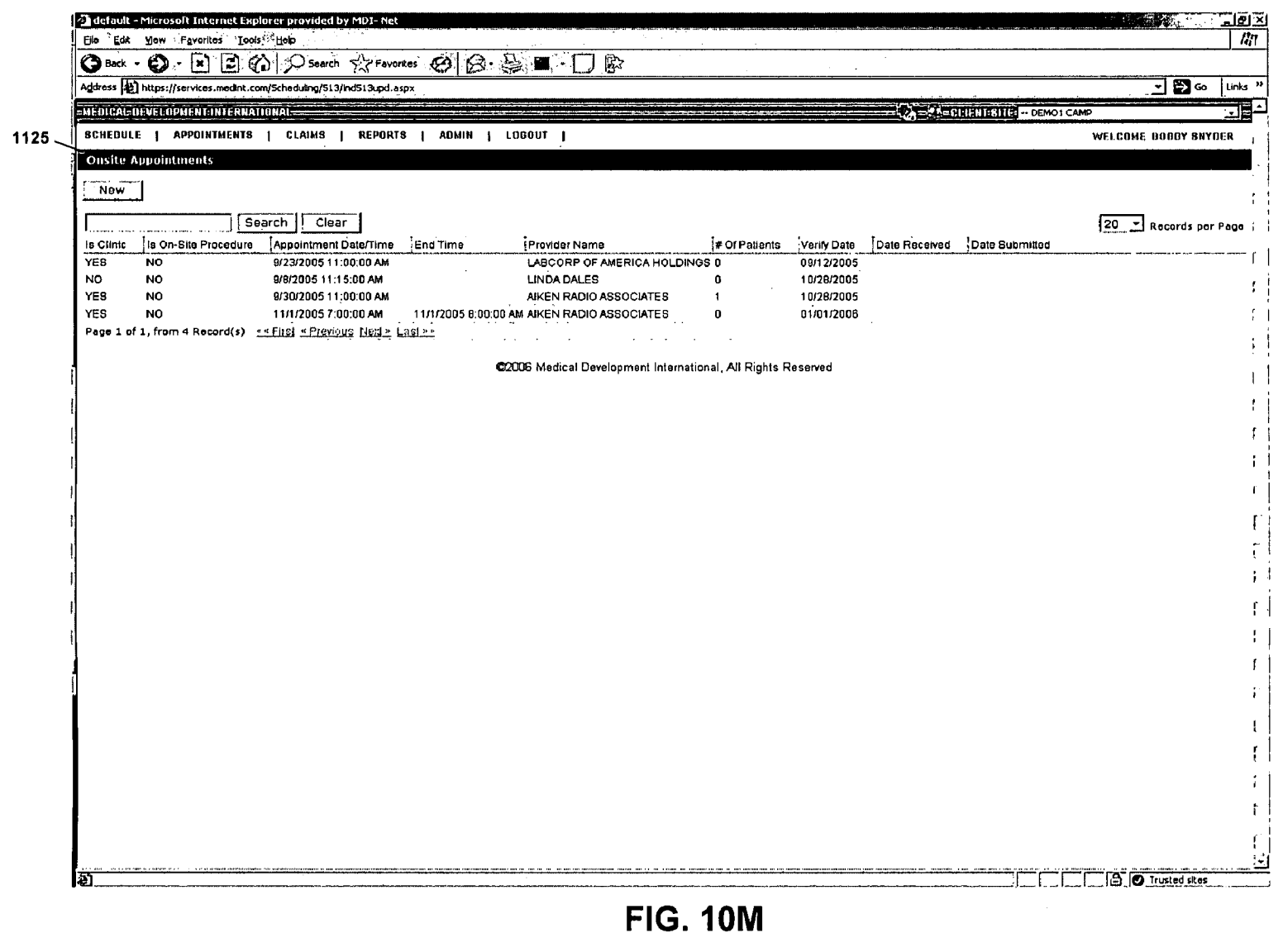
Figure 10N:
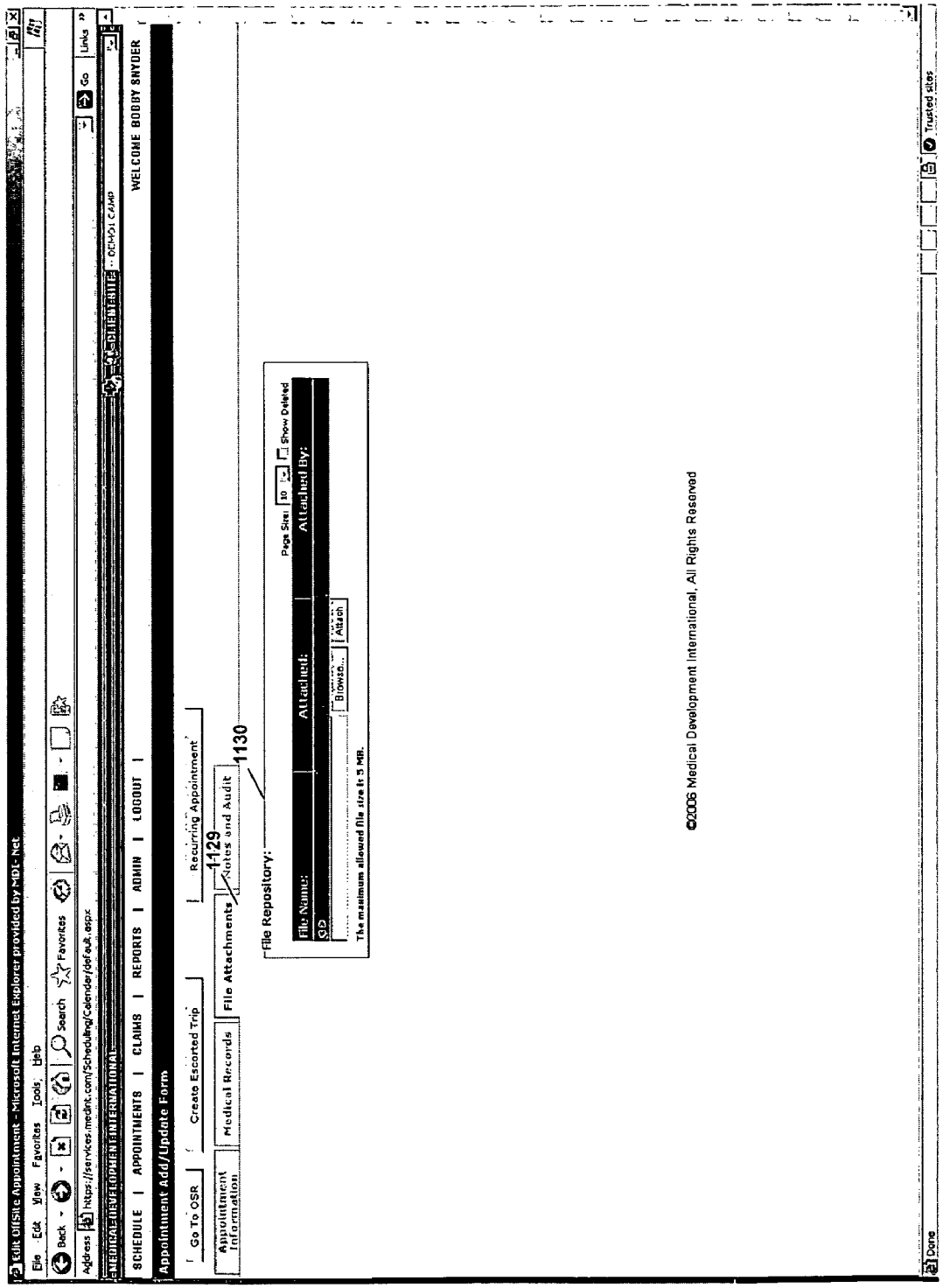
Figure 10O:
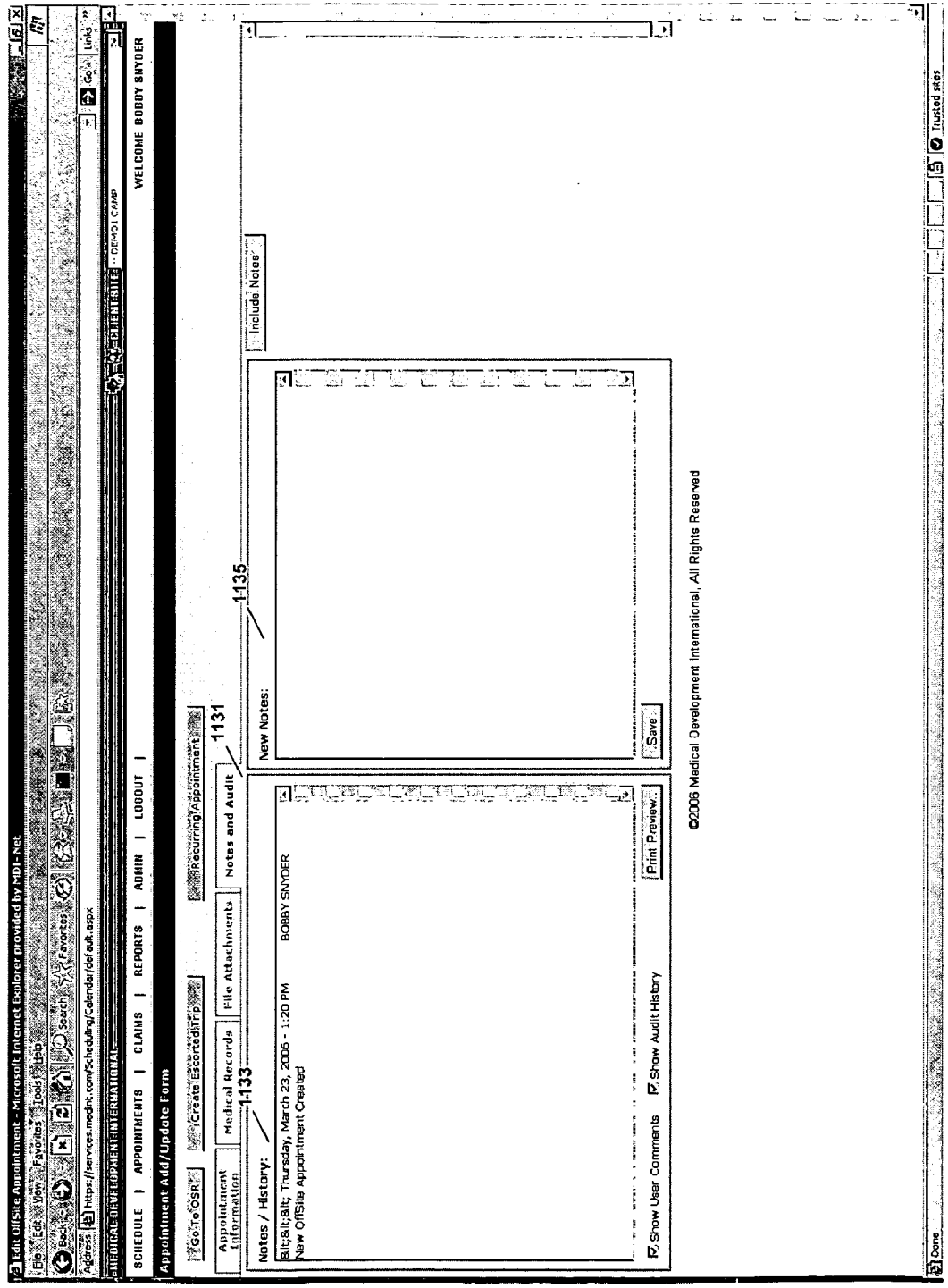
Figure 10P:
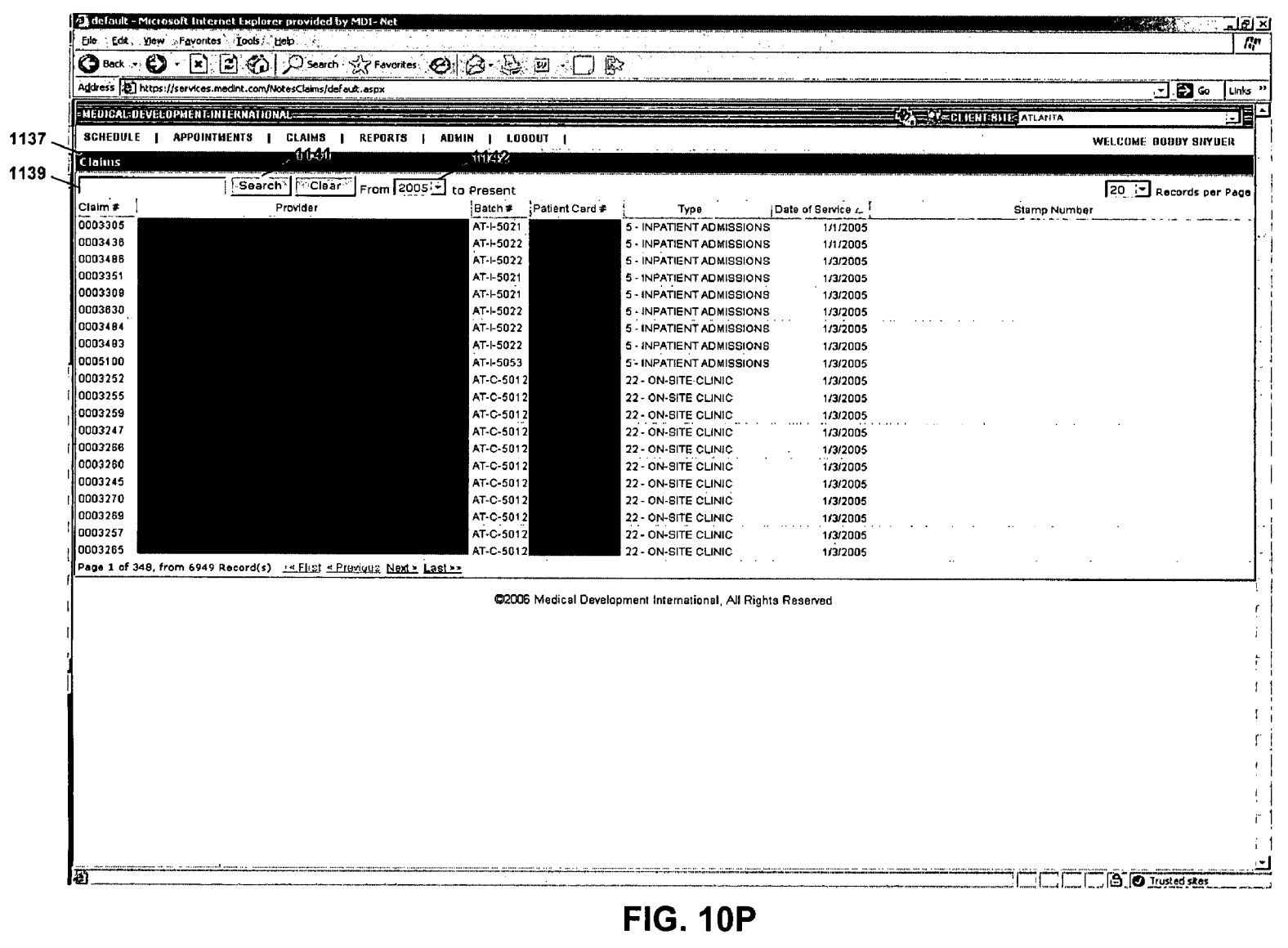
Figure 10Q:
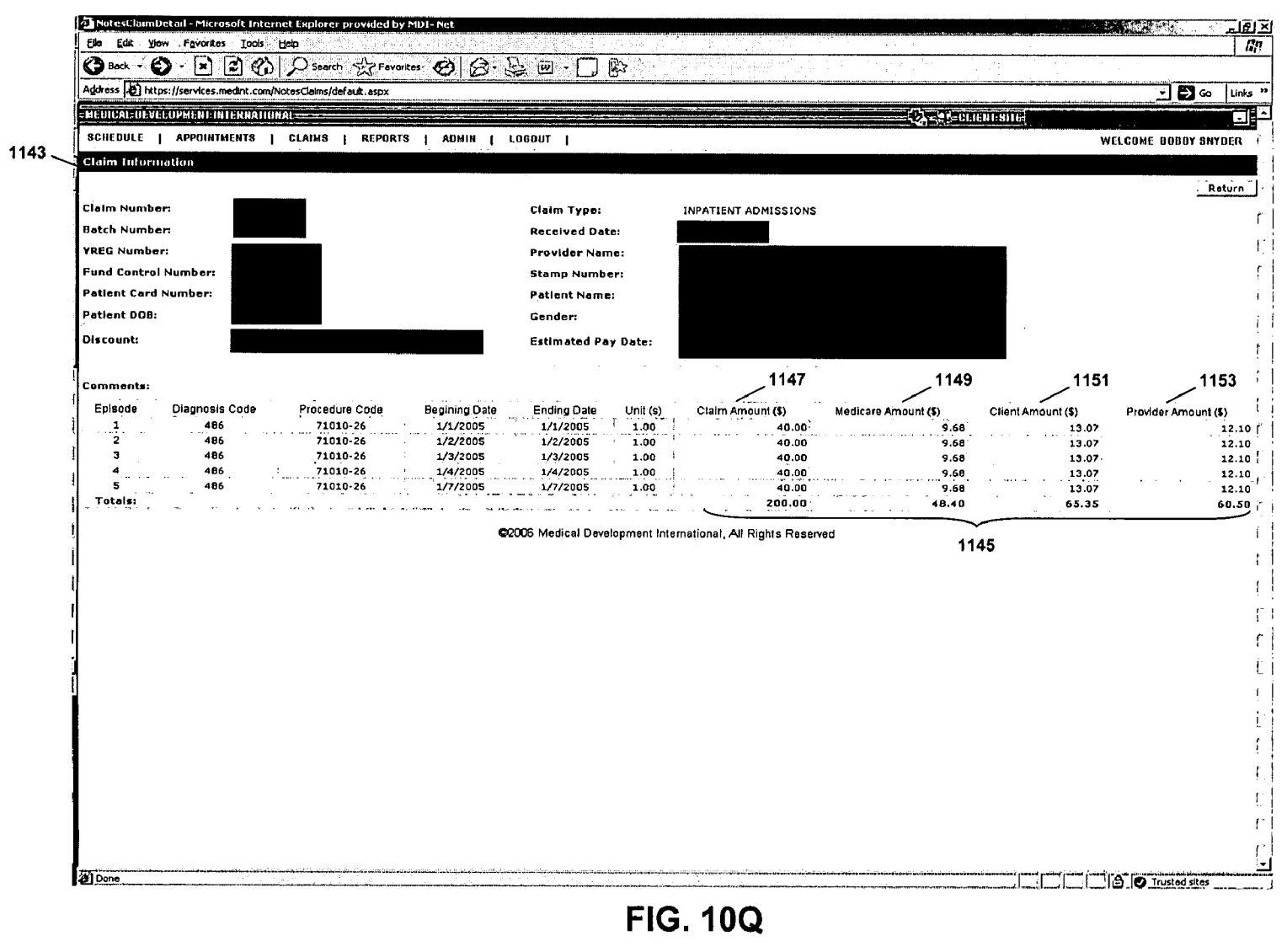
Figure 10R:
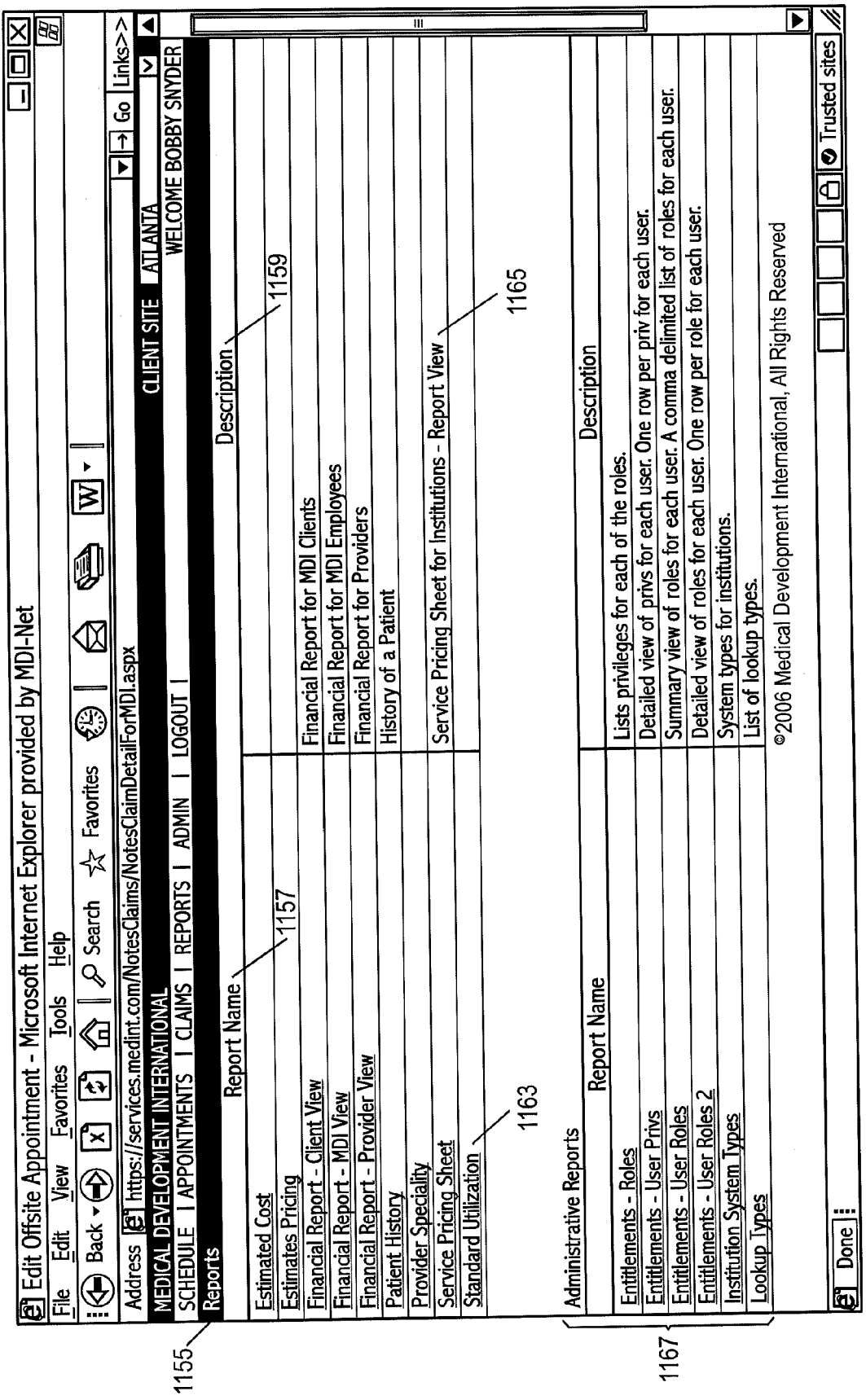
Figure 10S:
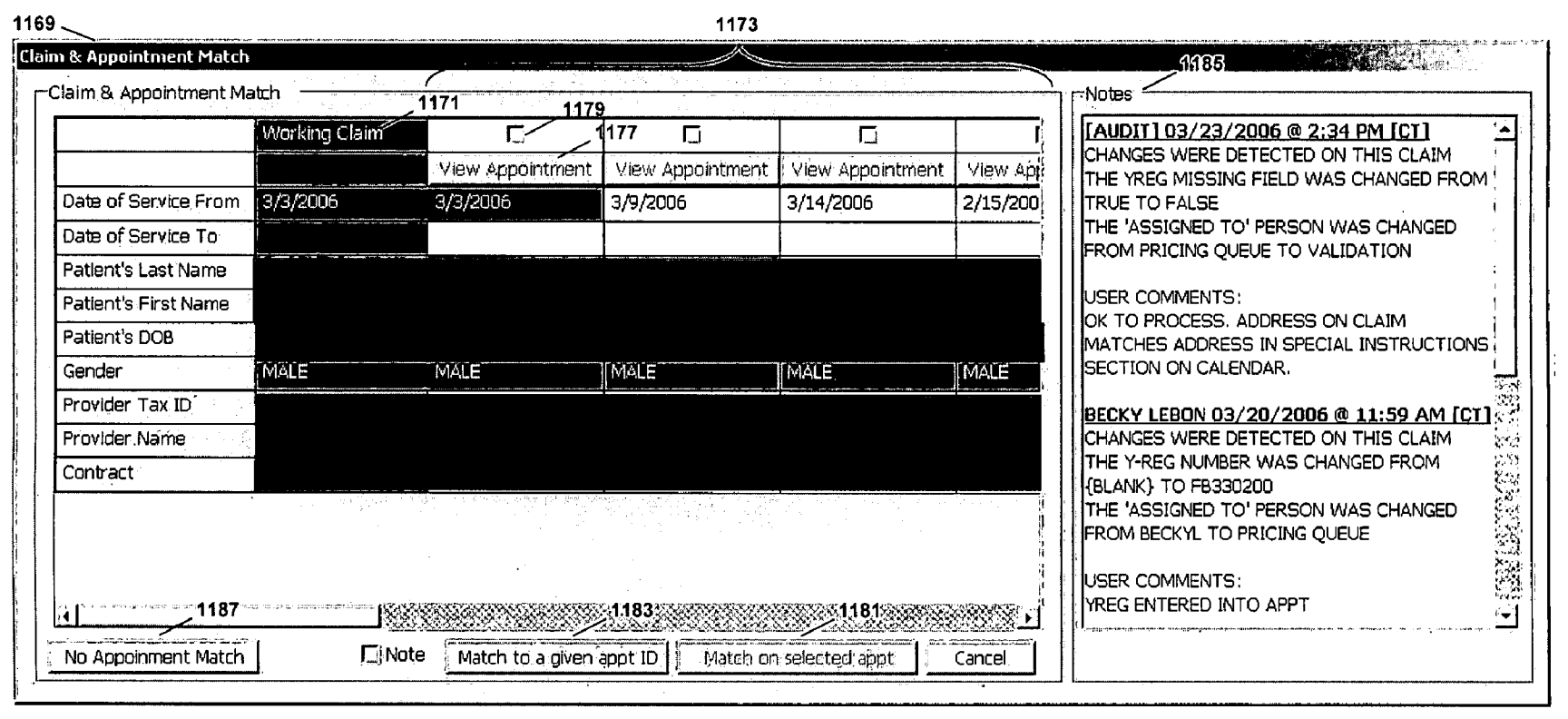
Figure 10V:
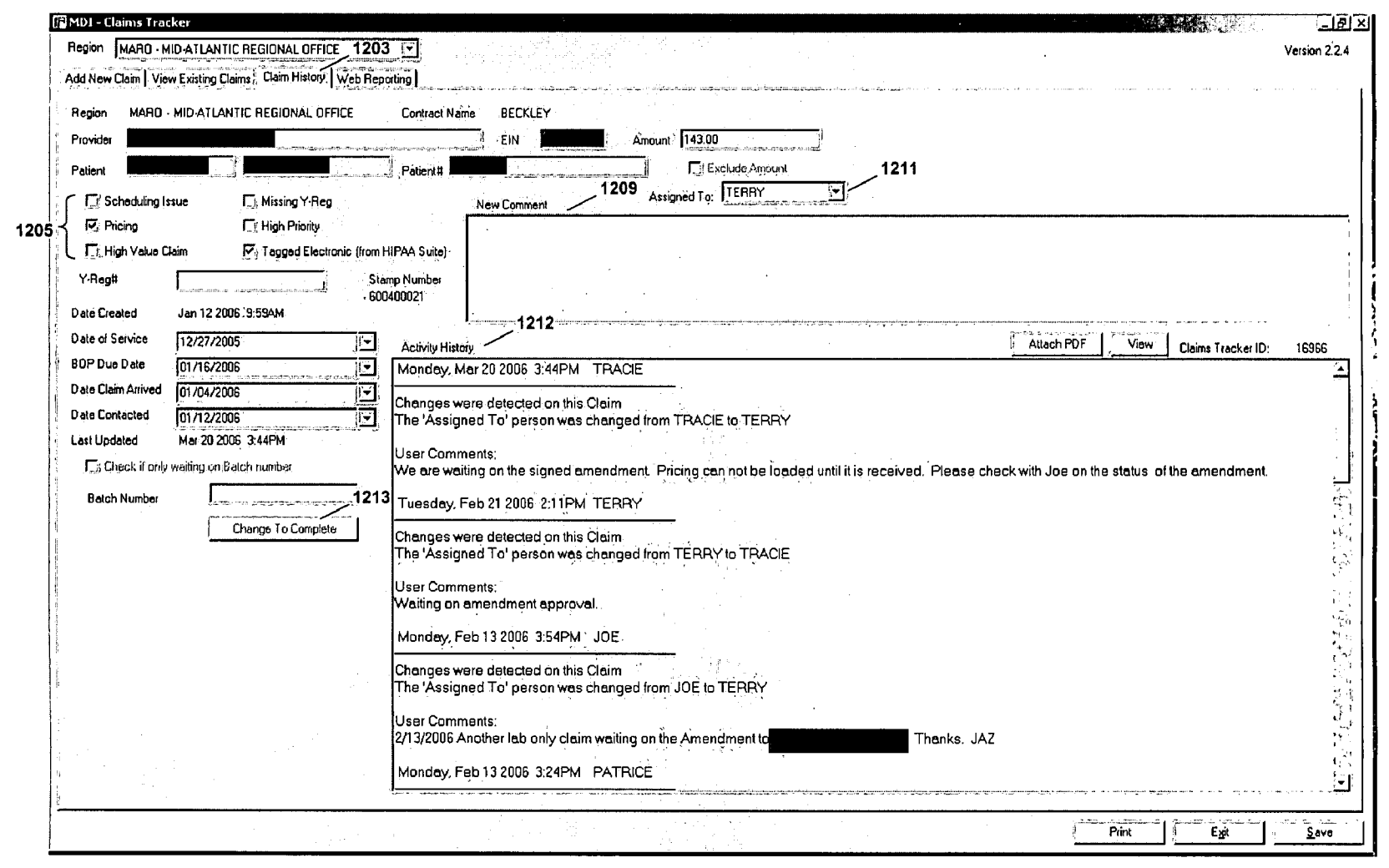
Figure 10X:
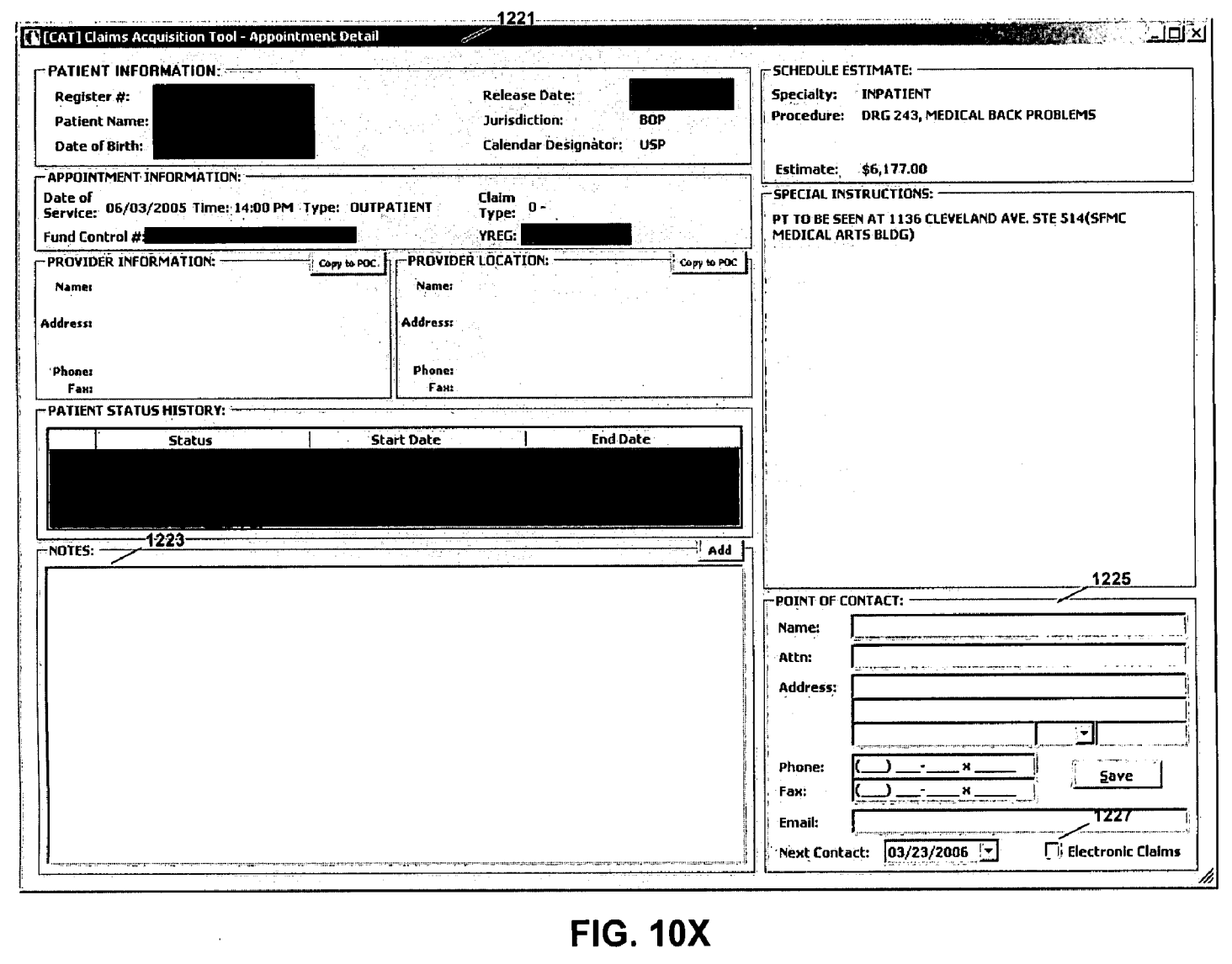

FIGS. 10A-10R show images of an example web-based scheduling tool that includes a scheduling module, an appointments module, a claims module, a reports module, and an administrator module. To ensure security, the web-based scheduling tool can be implemented with Secure Sockets Layer (SSL) technology to encrypt information and provide authentication. Persons of skill in the relevant art(s) will understand that the scheduling tool need not be web-based and can be implemented in a secure closed network.

Scheduling Module

When the client institution has a patient in need of medical services, the client can complete a referral request. Using the scheduling module, the client can enter patient information. FIG. 10A shows a Patient Information dialog box 1001, which is a portion of the scheduling module accessible at the client institution. In particular, the client can enter a code identifying the patient. In the example shown in FIG. 10A, the client enters a Register Number 1003, which is a unique number assigned to an inmate that remains associated with the inmate whenever incarcerated. If the patient's code has previously been entered into the scheduling module it can be stored indefinitely and the scheduling module can automatically complete the remaining fields of patient information. Conveniently, the scheduling module can be implemented to poll the client institution to check for information required to complete the fields to save the client time in completing the Patient Information section 1001.

If the patient's code has not been previously entered into the scheduling module, the client can complete the remaining patient information fields shown in FIG. 10A, including name, gender, jurisdiction (i.e., the name of the organization responsible for the patient, such as the Bureau of Prisons (BOP), the U.S. Marshall Service, etc.), calendar designator (i.e., on which calendar the appointment should be displayed, as will be described in more detail below), date of birth, and release date from the correctional institution (i.e., so that the institution does not pay for services rendered after the patient had been released or leaves the institution). Persons of skill in the relevant art(s) will understand that the scheduling module can be implemented with other patient information fields not shown in the example of FIG. 10A. Additionally, as shown in FIG. 10A, patient information fields can be implemented as drop-down menus 1004 listing available options for completing a particular field, and links to a viewable calendar 1005 can be provided for convenient selection of particular dates. Furthermore, in addition to completing the patient information fields, the client can also attach pertinent patient files, such as x-ray films, etc.

Using the scheduling module, the client can then enter patient appointment information. FIG. 10B shows a Patent Appointment Information dialog box 1007, which is another portion of the scheduling module accessible at the client institution. In particular, the client can provide an expenditure authorization code 1009. In the example of FIG. 10B, the client provides a "YREG," which is an authorization code specific to the BOP. In this case, the client has the option of selecting a checkbox 1011 to have the scheduling module automatically fill in the most recently used YREG. Other clients might provide a purchase order number, etc. instead of a YREG. The client also has the option of entering a client-specific Suffix 1013 to help the client further track the patient (e.g., the suffix might indicate a security level associated with an inmate, a level of billing, or any other client-defined field). The client can also enter an Appointment Time Frame 1014 to indicate a desired time frame for the appointment (e.g., one week, next month, as soon as possible, patient taken to emergency room, etc.). As shown in FIG. 10B, the Appointment Time Frame field 1014 can be implemented as a drop-down menu for faster completion. The client also has the option of entering in the Pertinent Information field 1015 any pertinent information about the patient (e.g., to explain why the patient was submitted to the emergency room or needs to see a particular specialist, or to include other notes, such as the reminder shown in FIG. 10B).

Also shown as part of the Patient Appointment Information dialog box 1007, is a Preliminary Estimate field 1017. Here the client can select a particular Specialty from a drop-down menu 1019 and a corresponding Procedure from a nested drop-down menu of procedures 1021 available for the selected specialty. Based on these selections, the scheduling module can automatically generate a preliminary estimate (e.g., $59.00 is this example) of the cost for the selected specialty/procedure combination that the client can use for planning and/or authorization purposes.

Having entered the pertinent patient and appointment information, the client can forward the referral request to a Central Scheduler of the scheduling module. In the example of FIG. 10B, the client can select the Create OSR link 1023 to forward the off-site referral (to request an appointment with a service provider to see the patient off-site) or on-site referral (to request an appointment with a service provider to see the patient on-site), both referred to herein as OSRs, to the Central Scheduler. The scheduling module can be configured to automatically assign a unique referral identification code to each OSR and generate an electronic OSR that is forwarded to the Central Scheduler.

Using the scheduling module, a scheduler can create an appointment based on the OSR. FIG. 10C shows a View OSR dialog box 1025, which is a portion of the scheduling module accessible at the Central Scheduler through which a scheduler (or other user) can View, Edit, Attach Consult, Schedule Appointment, Create Queue, Print, and Cancel particular OSRs. FIG. 10C shows an example electronic OSR 1027 that includes a contact information field 1029 for the client institution Contract Manager, a contact information field 1031 for the Central Scheduler Primary Contact, and a patient information field 1033 (i.e., Inmate Information in this example) and a Pertinent Information field 1035, which include information previously entered by the client institution.

By selecting the Attach Consult button 1037, the scheduler/user can attach to an appointment a consultation sheet, such as a Standard Form (SF) 513, which is a form the client institution can complete to communicate the patient's condition directly to the service provider. The scheduling module can store images of attached consultation sheets. In this way, the scheduler/user can not re-write the verbiage of the form, potentially reducing possible liability for treatment error. Optionally, the client institution can use the scheduling module to access and complete an electronic Consultation Sheet 1039, as shown in FIG. 10D, which can then be printed and submitted to the contract manager electronically, by facsimile, by paper mail, or by any other suitable manner of submission.

The Central Scheduler can create a queue of OSRs that have been submitted by the client. A scheduler is then responsible for contacting a service provider in a network of service providers affiliated with the client to schedule an appointment in accordance with each OSR. From the View OSR dialog box 1025 described above, the scheduler can select the Schedule Appointment button 1041 to enter appointment information for a particular OSR. FIG. 10E shows a Scheduling Information dialog box 1043 of the Central Scheduler, through which the scheduler completes various appointment information fields. The client might have scheduling rules that the scheduler should consider when making the appointment with the service provider, which are displayed in the Institution Scheduling Rules field 1045. Any pertinent information that was entered by the client is displayed in the Pertinent Information field 1047. FIG. 10F shows a Contract Manger dialog box 1049 through which the contract manger can communicate notes to the scheduler by completing the Note to Scheduler field 1051. These notes appear in the Scheduler Notes field 1053 of the Scheduling Information dialog box 1043, shown in FIG. 10E. Similarly, the scheduler can communicate any special instructions to the contract manger and others by completing the Special Instructions field 1055, also shown in FIG. 10E.

Among other information shown in FIG. 10E (i.e., Referred By, Requested Appointment Date, and Specialty), the scheduler can complete the Appointment Information fields 1057, such as an Appointment Type 1059 (e.g., Outpatient), Provider 1061, and Provider Location 1063. As shown in FIG. 10E, fields 1059-1063 can be implemented as drop-down menus for faster completion. The scheduler can also indicate whether the provider was contacted by selecting an appropriate Provider Contacted radio button 1065 (i.e., the scheduler might have left a message for the provider). Next the scheduler can complete the applicable Jurisdiction 1067 (e.g., Arkansas Dept. of Corrections (ADOC) in this example) and Calendar Designator 1068, which can be pre-selected based on the Patient Information 1001 entered by the client in FIG. 10A. Like the preliminary estimate calculated as shown in conjunction with the Patient Appointment Information dialog box 1007 in FIG. 10B, a Schedule Estimate 1069 can be automatically calculated for the particular specialty/procedure combination indicated (e.g., $59.00 for Radiology/X-Ray Leg in this example).

Additionally, the scheduler can select a unique Claim Type 1071, which can serve as an additional cross-check against corresponding Medicare codes during claim adjudication. After scheduling the appointment, the scheduler can enter the Appointment Date 1073, Appointment Time 1075, and estimate the Appointment Length 1077 and Appointment End Time 1079, which may be useful information for the client if the patient needs to be escorted to the appointment. Finally, the scheduling module typically is configured to automatically assign a unique Fund Control Number (FCN) 1081 to each appointment, which can serve as an additional cross-check against the corresponding fund authorization code (e.g., YREG code) during claim adjudication.

Advantageously, as shown in the Notes and Audit dialog box 1083 of FIG. 10G, the scheduling module can be configured to maintain a complete audit history of the scheduling process for each appointment. In the example of FIG. 10G, the Notes/History field 1085 indicates when an OSR was added to the Central Scheduler queue. Additionally, a user (i.e., scheduler, contract manager, etc.) can add notes in the New Notes field 1087 regarding a particular appointment that will subsequently appear in the Notes/History field 1085.

Appointments Module

After an appointment is scheduled, the appointments module can be configured to display the scheduled appointment on a calendar, which can be accessed by various users depending on established access rights. In an embodiment, when the appointments module displays a scheduled appointment on the calendar, the scheduling module removes the corresponding OSR from the Central Scheduler queue. FIG. 10H shows an exemplary view of a high-level calendar 1089, which displays numerous scheduled appointments. The appointments can be selectable so that a user can view and edit the corresponding appointment information. Calendar views can be customized according to the different types of users so that only information pertinent to a particular user is displayed for that user.

FIG. 10I shows an exemplary Appointment Add/Update Form 1091, through which a user can modify and save, cancel or print the appointment information for a selected appointment. Appointment information can be modified by completing the various fields shown in the Appointment Information dialog box 1099, including patient information fields 1101, appointment information fields 1103, service provider information fields 1105, Special Instructions field 1107 (to modify any special instructions entered via the Special Instructions field 1055 of the Scheduling Information dialog box 1043 of FIG. 10E), Schedule Estimate fields 1109, and discharge information fields 1111 (because the client institution should not pay for services rendered after the patient is discharged from the institution). Additionally, the user can add patient status history information via the Patient Status History field 1113. For example, if the patient goes the hospital, it might be useful to track when the patient's status changes from "emergency room" to "in-patient," etc.

For some clients, such as the BOP, the patient might need to be escorted by a guard or other security personnel to the scheduled appointment. In this case, the client can access the appointments module to download and complete an escorted trip form. Typically, these forms are printed and circulated for signatures at the client institution. As shown in FIG. 10I, the client can select the Create Escorted Trip button 1093 to download and complete an escorted trip form. An exemplary escorted trip form 1095 is shown in FIG. 10J. Also, for some requested procedures, such as dialysis, multiple appointments with the service providers might be required. Thus, as shown in FIG. 10I, a user can select the Recurring Appointment button 1097 to schedule all appointments associated with a particular OSR. These appointments would optimally be displayed in the same manner as other scheduled appointments as described below.

In addition to using the appointments module to view scheduled appointments on the calendar, a user can use the appointments module to filter and sort the scheduled appointments. For example, as shown in FIG. 10K, a user can choose from an Appointments drop-down list 1115 to view the calendar, On-Site scheduled appointments, or Off-Site scheduled appointments. FIG. 10L shows an example listing 1117 of Offsite Appointments. Using the drop-down menu 1119, a user can choose to view open appointments (shown in this example), active appointments, re-scheduled appointments, canceled appointments, etc. Additionally, the user can enter a search term in the search field 1121 and select the Search button 1123 to search all appointments for particular appointment information, such as for a particular provider. A user can also sort all appointments by selecting a particular column of appointment information. For example, the user may sort the appointments according to Appointment Date. FIG. 10M shows an example listing 1125 of Onsite Appointments, which can be filtered, searched, and sorted in a manner similar to that described above for the Offsite Appointments listing 1117 shown in FIG. 10L.

The appointments module can also be configured to enable the scheduler/user to attach a patient's medical record to an appointment. As shown in FIG. 10K, the scheduler can select the Medical Records tab 1127 and browse a file repository 1128 for and attach a patient's medical records. In addition to medical records, the scheduler/user can attach other files relating to a particular appointment (e.g., x-ray films). As shown in FIG. 10N, the scheduler/user can select the File Attachments tab 1129 and browse the file repository 1130 for and attach other related files.

Like the scheduling module described above, the appointments module can advantageously maintain a complete audit history of the appointment creation process for each appointment. As shown in the Notes/History field 1133 of the Notes and Audit dialog box 1131 of FIG. 10O, the audit history can reflect when a new appointment is created. The audit history can also reflect when an appointment is modified, canceled, the patient is a no-show, etc. Additionally, a user (i.e., scheduler, contract manager, etc.) can add notes in the New Notes field 1135 regarding a particular appointment to subsequently be displayed in the Notes/History field 1133.

Claim Intake Module

Claims from service providers relating to scheduled appointments are received and processed to capture claim information. As described above with respect FIGS. 1-8, service information from non-electronic claims can be manually captured, while service information from electronic claims can be automatically captured. In the case of manual entry, the double-blind entry process described above can be implemented to detect and correct keying errors. In both cases, an image of the received claim can be generated and attached to each claim record. Discrepancies are then identified and resolved, usually by a third person, particularly when the discrepancy is not automatically resolvable through spell-checker or grammar-checker software components. Advantageously, when used in conjunction with the windows-based adjudication tool, which is described in detail below, to link captured service information with corresponding appointment information, the claims module can provide a user with significantly more information than conventional disparate appointment scheduling and claim processing applications.

Users, such as the client institution, service providers, and schedulers, can use the claims module to filter and sort processed claims and select particular claims to view corresponding service information. For example, FIG. 10P illustrates a Claims dialog box 1137, in which processed claims are displayed. Using a drop-down menu 1142, processed claims from a particular year to present can be displayed. Corresponding service information, such as Claim Number, Provider and Date of Service, etc., can be organized in columns (note that some of the data has been redacted). The user can enter a search term in the search field 1139 and select the Search button 1141 to search all claims for particular service information, such as a particular service provider. A user can also sort all claims by selecting a particular column of service information. For example, the user may sort the claims according to Date of Service.

A user can select a particular claim to view detailed service information for the selected claim. For example, FIG. 10Q shows a Claim Information dialog box 1143 that includes captured service information (note that some of the data has been redacted) for a selected claim. The claims module can be configured to selectively display claim amount information 1145 based on the user. For example, if the user is the scheduler, the scheduler should be able to view all of the claim amount information, including Claim Amount 1147 (i.e., the amount submitted by the service provider), the Medicare Amount 1149 (i.e., the amount Medicare would cover for the claimed procedure), the Client Amount 1151 (i.e., the amount the client institution pays), and the Provider amount 1153 (i.e., the amount paid to the service provider). A service provider should be able use the claims module to view and sort claims that the service provider has submitted but should not be able to view the Client Amount 1151. Likewise, a client institution should be able to use the claims module to view claims associated with its patients but should not be able to view the Provider Amount 1153.

Reports Module

The reports module can be used to generate predefined proprietary or ad hoc reports based on individual or aggregated service information captured from processed claims. FIG. 10R shows a Reports dialog box 1155 that identifies by Report Name 1157 and Description 1159 various reports that can be generated. For example, proprietary reports associated with particular client institutions can be generated to provide such information as the number of OSRs generated, the number of appointments scheduled, canceled, re-scheduled, etc., and aggregated financial information such as the total claim amount, the total savings, and the percentage of savings. The Standard Utilization report 1163 is an example report that allows a user to add filters and sort on any of the information captured by the web-based scheduling tool. For example, the client institution might generate a report for all of the scheduled pathology appointments, showing aggregated financial information, such as the total pathology claim amounts, the pathology claim histories, etc.

The reports module can also be used to access a Service Pricing Sheet 1165 for a particular client institution. For example, by viewing the Service Pricing Sheet 1165, the client institution can quickly review the pricing structures of their provider networks. The reports module can also be used to generate various Administrative reports 1167, as shown in FIG. 10R, which can be used to identify user roles and privileges with respect to the web-base scheduling tool. The web-based scheduling tool further includes an administrator module that an administrator can use to define user roles and access privileges associated with the various modules, as well as to define and modify the provider networks and corresponding service providers.

Windows-Based Adjudication Tool

As described above, the web-based scheduling tool can be configured to track information throughout the entire appointment process, from the referral request, to a scheduled appointment, to a processed claim. The windows-based adjudication tool, which is described in detail below, can advantageously be configured to use the tracked information to determine the appropriateness of claims received from service providers. FIGS. 10S-10V show images of an example windows-based adjudication tool that includes an adjudication module and a claim tracker module.

Persons of skill in the relevant art(s) will understand that the adjudication tool need not be windows-based and can instead be implemented as a secure web-based application.

Adjudication Module

Conventional claims processing systems typically provide little protection against fraudulent and erroneous claims. To reduce the number of fraudulent and erroneous claims being paid, the adjudication module can advantageously determine the appropriateness of the received claims by only submitting for payment received claims that can be matched to scheduled appointments. Unlike conventional disparate appointment and claim processing systems and methods, the integrated scheduling and adjudication tools described herein can be configured to quickly and accurately determine the appropriateness of the received claims.

The adjudication module can queue received claims in an adjudication queue and intelligently serve up unverified claims from the queue to available adjudicators for validation. An adjudicator can initiate a search for candidate appointments that match a particular received claim. The adjudication module can use logic, fuzzy logic and/or AI to compare the service information associated with the particular received claim to the appointment information associated with each of the scheduled appointments, and can weight each scheduled appointment based on a degree of similarity to the particular received claim. The adjudication module can also perform a duplicate check before or after the appointment match to determine whether the particular received claim is a duplicate of an already processed claim and to identify services of the particular received claim that are duplicate services (i.e., multiple claims might be received for one appointment and the same service might be identified in more than one of the claims). The adjudication process is described in more detail above in conjunction with FIGS. 1-8.

FIG. 10S shows an exemplary Claim & Appointment Match dialog box 1169 of the adjudication module in which a particular received claim can be identified in the Working Claim field 1171 and several candidate appointments 1173 can be displayed according to degree of similarity next to the working claim, with the best match occupying the first position adjacent to the working claim, and so forth. The accuracy of the adjudication module can be such that most of the time the correct appointment is placed in the first position adjacent to the working claim.

In the event that the adjudication module determines that an appointment perfectly matches the working claim, the adjudication module can be configured to display the perfectly matching candidate appointment differently, for instance by highlighting the perfectly matching candidate appointment in a particular color. The adjudicator can manually validate the working claim by selecting a View Appointment button 1177 to view the appointment information corresponding to the candidate appointments and determine which one of the candidate appointments, if any, matches the working claim. The adjudication module can alternatively be configured to automatically validate claims for which a perfectly matching candidate appointment is identified so that the adjudicator need only manually validate those claims for which no perfectly matching appointments are identified.

As further shown in FIG. 10S, after the adjudicator identifies a candidate appointment that matches the working claim, the adjudicator can select the candidate appointment using the appropriate checkbox 1179 and the Match On Selected Appointment button 1181. If the adjudicator determines that an appointment having a particular unique appointment identifier code matches the working claim, the adjudicator can select the Match To A Given Appointment ID button 1183 to digitally tie the unique claim identifier code of the working claim to the unique appointment identifier code of the matching appointment. If the adjudicator determines that none of the candidate appointments matches the working claim, the adjudicator can add a note defining the problem in the Notes field 1185 and select the No Appointment Match button 1187. In this case, the working claim can be "flagged" (i.e., identified in some fashion) as a problem claim and forwarded to the claim tracker module for resolution as described below.

FIG. 10T shows an example Verifying Digital Claim dialog box 1189 (note that some of the data has been redacted), which can be used to verify the service information associated with a particular claim, such as the Claim Amount 1191. Note that this verification step can be bypassed or omitted. The adjudication process ends when the adjudicator verifies the working claim and submits it for payment.

Claim Tracker Module

The windows-based adjudication tool can advantageously be configured to include a claim tracker module that intelligently routes a flagged claim to various trouble shooters in an attempt to resolve the problem in a timely manner (e.g., typically in as little as a few days for the claim tracker module, as opposed to a few months for conventional claim processing systems and methods). The trouble shooters can be grouped according to geographic regions and attempt to resolve the problems associated with the flagged claims in a queue of flagged claims for their particular region. For example, FIG. 10U shows an exemplary queue of open flagged claims 1193 for a particular region. A particular region can be selected using the drop-down menu 1195. In this case, the flagged claims for a Mid-Atlantic Regional Office (MARO) are displayed (note that some of the service information has been redacted).

The claim tracker module can also be configured to generate customized views based on the user. For example, the claim tracker module can be configured to only display the flagged claims forwarded to a particular adjudicator or contract manager, and not display all of the flagged claims to each user. As shown in FIG. 10U, the user can execute customized searches for flagged claims (e.g., flagged claims having a particular problem) using the search field 1197, and reorder the display of the flagged claims by sorting the flagged claims according to the various column categories (i.e., ID, Contract, Provider, EIN, Date of Service, Patient Number, Patient Last/First Name, Amount, etc.). The user can also select a particular View button 1199 to view a PDF file of a claim image and a particular Select button 1201 to select a particular flagged claim and take steps to resolve the identified problem.

FIG. 10V shows a Claim History dialog box 1203 of the claim tracker module for an exemplary flagged claim (note that some data has been redacted). The Claim History dialog box 1203 can display relevant appointment and service information associated with the flagged claim, including an indication of the particular problem 1205 (e.g., Pricing in this example). Each user can view an Activity History field 1212, which can indicate to whom the flagged claim has been routed, when it was routed, and what each user has done to try to resolve the problem. Each user that works on resolving the flagged claim can enter a comment in the New Comment field 1209 and assign the flagged claim to another user for further resolution by selecting a user from the Assigned To drop-down list 1211. In this way, the claim tracker module might motivate the users to work to resolve the flagged claims in a timely fashion, or at least might be used to identify where particular flagged claims are stymied.

For example, if the problem is no appointment was scheduled for the flagged claim (e.g., the patient had to go to the emergency room and the client institution did not have time to complete a referral request), then the trouble shooter might attempt to determine which client institution is associated with the flagged claim, and forward the flagged claim to the contract manager requesting that the contract manager complete a referral request so that an appointment can be created. In another example, if the problem is a pricing error (e.g., an appointment corresponds to the claim but the adjudicator could not find a contract with the service provider, who submitted the claim), the trouble shooter might forward the claim to the contract manager to work out the pricing problem. In other cases, the trouble shooter might forward the claim to the service provider, for example, if there is a Medicare problem (e.g., an incorrect Medicare code for the claimed service).

The claim tracker module can be configured with a reporting feature to periodically produce reports that monitor the progress of the different regions (e.g., the report can identify flagged claims for which no activity has occurred for several days, what flagged claims are being resolved by contract mangers, an average length of time the flagged claims have been in the claim tracker module, etc.). Such reports can be beneficial for expediting the time it takes to resolve the flagged claims so that service providers can get paid in a more timely fashion. A trouble shooter can indicate when the problem associated with a particular flagged claim is resolved by selecting the Change to Complete button 1213. In one embodiment, the claim tracker module can be configured to route the resolved flagged claim to the top of the adjudication queue so that it is validated by an adjudicator in an expedited fashion. Additionally, the claim tracker module can be configured to remove the claim from the flagged claim queue only after the adjudicator submits the resolved flagged claim for payment.

Claims Acquisition Tool

In addition to the scheduling and adjudication tools described above, a claims acquisition tool can be configured to identify appointments that have not been associated with particular received claims by the adjudication module. By identifying and resolving such appointments, the claims acquisition tool can recover claims for the service providers, making it more advantageous for the service provider to contract with the client institution.

Based on the appointment information, the claims acquisition tool can be configured to determine what type of claim is anticipated for a particular appointment. In this way, if no claim is received within a predetermined time period after the appointment is to have occurred, a trouble shooter can contact the service provider with whom the appointment was scheduled and determine whether the service provider has already submitted or is going to submit a corresponding claim. The claims acquisition tool can also be configured to analyze the appointment information and determine how many claims are anticipated to be received for a particular appointment (i.e., for some appointments, multiple claims from one or more service providers might be anticipated due to various procedures being performed at the appointment). In this way, if the anticipated number of claims is not received within a predetermined time period after the appointment is to have occurred, a trouble shooter can contact the service provider(s) with whom the appointment was scheduled and determine whether the service provider has already submitted or is going to submit an anticipated claim.

Like the claim tracker module described above, the claims acquisition tool can be configured to maintain a working list of appointments for which claims are expected. After the adjudication module associates a particular received claim with an appointment in the claims acquisition tool list, the appointment can be removed from the list. FIGS. 10W and 10X show images of an example windows-based claims acquisition tool. Persons of skill the relevant art(s) will understand that the claims acquisition tool need not be limited to a windows-based implementation, and can also be implemented in a web-based environment. FIG. 10W shows an exemplary list of Appointments without claims 1215 for a particular Contract/Institution that can be selected from a drop-down menu 1217 (note that some of the data has been redacted). A trouble shooter can execute customized searches for particular types of appointments using the search field 1219 and reorder the display of the appointments by sorting the appointments according to the various column categories (i.e., Appointment ID, Appointment Date, Age, Patient Name, Provider Name, Scheduled Estimate, YREG, Last Contact, Next Contact, etc.). The trouble shooter can also select a particular appointment and view the associated appointment information.

FIG. 10X shows an Appointment Detail dialog box 1221 for an exemplary appointment without a claim that includes the associated appointment information. Via the Appointment Detail dialog box 1221, the trouble shooter can add notes (e.g., to request information) by completing a Notes field 1223, and save new points of contact by completing a Point of Contact field 1225 (e.g., when the original point of contact for a provider is no longer valid and the new point of contact needs to be notified that a claim should be submitted for the appointment). The trouble shooter can also indicate whether electronic claims are expected to be submitted by selecting the Electronic Claims checkbox 1227 (service providers are encouraged to submit claims in electronic format because electronic claims are less likely to be lost than non-electronic claims and are therefore more likely to be paid reliably). By integrating the claims acquisition tool with the scheduling and adjudication tools described above, problem claims are more likely to be identified and resolved in a timely fashion.

CONCLUSION

The present invention has been described with reference to several exemplary embodiments, however, it will be readily apparent to persons of skill in the relevant art(s) that it is possible to embody the invention in specific forms other than those of the exemplary embodiments described above. This may be done without departing from the spirit of the invention. These exemplary embodiments are merely illustrative and should not be considered restrictive in any way. The scope of the invention is given by the appended claims, rather than the preceding description, and all variations and equivalents which fall within the range of the claims are intended to be embraced therein.

What is claimed is:

1. A system for determining the appropriateness of service provider claims for payment, comprising:
   a scheduling module configured to schedule appointments in a computer for patients with service providers based on requests for services, wherein the scheduling module is further configured to generate appointment information corresponding to each of the scheduled appointments;
   a claim intake module configured to receive claims from the service providers for payment of charges associated with services rendered by the service providers to the patients, wherein the claim intake module is further configured to capture service information in a computer corresponding to each of the received claims; and
   an adjudication module configured to automatically identify in a computer candidate appointments that correspond to a particular received claim based on a degree of similarity between the service information associated with the particular received claim and the appointment information associated with the scheduled appointments, wherein the adjudication module is further configured to present the particular received claim for payment when at least one of the candidate appointments corresponds to the particular received claim and flag in a computer the particular received claim for resolution when none of the candidate appointments corresponds to the particular received claim.

2. The system of claim 1, wherein the scheduling module further comprises a calendar interface configured to display the scheduled appointments as selectable elements for accessing corresponding appointment information.

3. The system of claim 1, wherein each request for services includes a patient identifier code.

4. The system of claim 1, wherein each request for services includes an authorization code.

5. The system of claim 1, wherein the appointment information includes at least one unique service identifier code for each requested service.

6. The system of claim 1, wherein the appointment information includes a unique appointment identifier code.

7. The system of claim 6, wherein the service information includes a unique claim identifier code.

8. The system of claim 7, wherein the adjudication module is further configured to associate the unique claim identifier code of the particular received claim to the unique appointment identifier code of the candidate appointment that corresponds to the particular received claim.

9. The system of claim 1, wherein the appointment information includes one or more associated file attachments.

10. The system of claim 1, wherein the appointment information includes communication between a system operator and a service provider.

11. The system of claim 1, wherein the service information includes an image of the received claim.

12. The system of claim 1, further comprising an administrator module configured to modify a list of service providers in a network.

13. The system of claim 1, further comprising an administrator module configured to modify access rights to the system.

14. The system of claim 1, further comprising a reporting module configured to generate reports based on aggregated service information.

15. The system of claim 1, further comprising a reporting module configured to identify a pricing structure in a computer by displaying the pricing of services for each provider within a network of service providers.

16. The system of claim 1, further comprising a claim tracking module configured to route flagged claims in a computer from the adjudication module to at least one trouble shooter for resolution.

17. The system of claim 16, wherein the claim tracking module is further configured to compile a history of the routing.

18. The system of claim 16, wherein the claim tracking module is further configured to route resolved flagged claims to the adjudication module for validation ahead of other claims.

19. The system of claim 1, further comprising a claim acquisition module configured to automatically determine in a computer which scheduled appointments have not been identified by the adjudication module as corresponding to particular received claims within a predetermined period of time.

20. The system of claim 19, wherein the claim acquisition module is further configured to queue the scheduled appointments which have not been identified by the adjudication module as corresponding to particular received claims within a predetermined period of time for resolution by at least one system operator.

21. The system of claim 20, wherein the claim acquisition module is further configured to remove a scheduled appointment from the queue when a received claim is identified that corresponds to the scheduled appointment and the identified received claim is forwarded to the adjudication module.

22. The system of claim 20, wherein the claim acquisition module is further configured to automatically determine a number of received claims associated with a particular scheduled appointment and queue the particular scheduled appointment for resolution by the system operator when the adjudication module has identified the particular scheduled appointment as corresponding to fewer than the number of received claims within the predetermined period of time.

23. A method for determining the appropriateness of service provider claims for payment, comprising:
scheduling appointments for patients with service providers based on requests for services;
generating appointment information corresponding to each of the scheduled appointments;
capturing in a computer, service information corresponding to claims received from the service providers for payment of charges associated with services rendered by the service providers to the patients;
automatically identifying in a computer, candidate appointments that correspond to a particular received claim based on a degree of similarity between the service information associated with the particular received claim and the appointment information associated with the scheduled appointments;
flagging in a computer, the particular received claim for resolution when none of the candidate appointments corresponds to the particular received claim; and
presenting the particular received claim for payment when at least one of the candidate appointments corresponds to the particular received claim.

24. The method of claim 23, wherein the step of scheduling comprises creating a referral for each of the requests.

25. The method of claim 24, wherein the step of scheduling further comprises assigning a unique referral identification code to each referral.

26. The method of claim 24, wherein the step of scheduling further comprises queuing the referrals in a centralized scheduling queue.

27. The method of claim 26, wherein the step of scheduling further comprises selecting a referral from the centralized scheduling queue and scheduling an appointment for the selected referral.

28. The method of claim 23, wherein the step of scheduling comprises scheduling appointments with service providers identified in a particular network of service providers.

29. The method of claim 23, wherein the step of scheduling comprises scheduling the appointments in accordance with one or more predefined scheduling rules.

30. The method of claim 23, wherein the step of generating appointment information comprises selecting the appointment information from predefined menus of appointment information.

31. The method of claim 23, wherein the step of generating the appointment information comprises calculating a price estimate for a particular requested service.

32. The method of claim 23, wherein the step of generating the appointment information comprises selecting a unique service identifier code for each requested service.

33. The method of claim 23, wherein the step of generating the appointment information comprises assigning a unique appointment identifier code to each of the scheduled appointments.

34. The method of claim 23, wherein the step of generating the appointment information comprises maintaining an audit history for each of the scheduled appointments.

35. The method of claim 23, wherein the step of generating the appointment information comprises attaching associated information files.

36. The method of claim 23, further comprising displaying each scheduled appointment using a calendar interface such that each displayed scheduled appointment can be selected to access corresponding appointment information.

37. The method of claim 23, further comprising sorting the scheduled appointments based on categories of the appointment information and selecting a particular sorted scheduled appointment to view corresponding appointment information and to modify the corresponding appointment information as required.

38. The method of claim 23, wherein the capturing service information step comprises automatically populating a database with service information corresponding to claims received in an electronic format from the service providers.

39. The method of claim 23, wherein the capturing service information step comprises manually entering into the database service information corresponding to claims received in a non-electronic format from the service providers.

40. The method of claim 39, wherein the capturing service information step further comprises manually entering the service information into the database in accordance with a double-blind entry process comprising two data entry personnel entering the same service information wherein neither data entry person observes the data input by the other.

41. The method of claim 39, wherein the capturing service information step further comprises storing in the database images of the claims received in a non-electronic format.

42. The method o claim 23, further comprising sorting the received claims based on categories of the serviced information and selecting a particular received claim to view corresponding service information.

43. The method of claim 23, further generating one or more reports based on aggregated service information.

44. The method of claim 23, wherein the step of automatically identifying candidate appointments comprises routing the particular received claim from an adjudication queue to an initial adjudicator, wherein the particular received claim is routed to another adjudicator if the initial adjudicator does not respond within a predetermined period of time.

45. The method of claim 23, further comprising:
automatically identifying candidate claims that correspond to a particular received claim based on a degree of similarity between the service information associated with the particular received claim and the service information associated with the received claims;
determining the particular received claim is a duplicate claim by analyzing the identified candidate claims; and
flagging duplicate claims for resolution.

46. The method of claim 45, wherein the step of determining if the particular received claim is a duplicate claim comprises automatically determining if the particular received claim is a duplicate claim.

47. The method of claim 23, wherein the step of automatically identifying candidate appointments comprises displaying the candidate appointments for review by an adjudicator, wherein the adjudicator determines whether to flag the particular received claim for resolution or to present the particular received claim for payment.

48. The method of claim 47, wherein the step of displaying candidate appointments for review by an adjudicator comprises displaying candidate appointments for review by an adjudicator when none of the candidate appointments directly corresponds to the particular received claim.

49. The method of claim 23, wherein the steps of flagging the particular received claim for resolution and presenting the particular received claim for payment comprise:
   automatically flagging the particular received claim for resolution when none of the candidate appointments corresponds to the particular received claim; and
   automatically presented the particular received claim for payment when at least one of the candidate appointments corresponds to the particular received claim.

50. The method of claim 23, wherein the step of flagging the particular received claim for resolution comprises routing the flagged claim to one or more trouble shooters for resolution.

51. The method of claim 50, further comprising compiling a history of the routing of the flagged claim among the trouble shooters.

52. The method of claim 50, further comprising routing resolved flagged claims to an adjudicator for validation ahead of other claims.

53. The method of claim 23, wherein the step of presenting the particular received claim for payment further comprises associating a unique claim identifier code of the particular received claim to a unique appointment identifier code of the candidate appointment that corresponds to the particular received claim.

54. The method of claim 23, wherein the step of presenting the particular received claim for payment further comprises reviewing a pricing signature for a service provider comprising unique information associated with a service provider that assists in verifying the correct pricing and corresponding to the particular received claim to verify a payment amount for services rendered by the service provider.

55. The method of claim 23, wherein the step of presenting the particular received claim for payment further comprises generating a submission report including information about the routing of the particular received claim from the time the service information corresponding to the particular received claim was captured to the time the particular received claim was presented for payment.

56. The method of claim 23, further comprising automatically detecting which scheduled appointments have not been identified as corresponding to any received claims within a predetermined period of time.

57. The method of claim 56, further comprising queuing the scheduled appointments which have not been identified as corresponding to any received claims within a predetermined period of time for resolution by at least one trouble shooter.

58. The method of claim 57, further comprising removing a scheduled appointment from the queue when a received claim is identified that corresponds to the scheduled appointment and the identified received claim is presented for payment.

59. The method of claim 57, further comprising automatically determining an anticipated number of received claims associated with a particular scheduled appointment and queuing the particular scheduled appointment for resolution by the trouble shooter when the particular scheduled appointment corresponds to fewer than the anticipate number of received claims within the predetermined period of time.

60. A non-transitory computer recording medium on which the method for determining appropriateness of service provider claims for payment is recorded as a program code that can be executed by a computer, the method comprising:
   scheduling appointments for patients with service providers based on requests for services;
   generating appointment information corresponding to each of the scheduled appointments;
   capturing in a computer, service information corresponding to claims received from the service providers for payment of charges associated with services rendered by the service providers to the patients;
   automatically identifying in a computer, candidate appointments that correspond to a particular received claim based on a degree of similarity between the service information associated with the particular received claim and the appointment information associated with the scheduled appointments;
   flagging in a computer, the particular received claim for resolution when none of the candidate appointments corresponds to the particular received claim; and
   presenting the particular received claim for payment when at least one of the candidate appointments corresponds to the particular received claim.

61. A system for determining the appropriateness of service provider claims for payment, comprising:
   means for scheduling appointments for patients with service providers based on requests for services;
   means for generating appointment information corresponding to each of the scheduled appointments;
   means for capturing service information corresponding to claims received from the service providers for payment of charges associated with services rendered by the service providers to the patients;
   means for automatically identifying candidate appointments that correspond to a particular received claim based on a degree of similarity between the service information associated with the particular received claim and the appointment information associated with the scheduled appointments;
   means for flagging the particular received claim for resolution when none of the candidate appointments corresponds to the particular received claim; and
   means for presenting the particular received claim for payment when at least one of the candidate appointments corresponds to the particular received claim.

* * * * *